United States Patent
Song

(10) Patent No.: US 9,725,507 B2
(45) Date of Patent: Aug. 8, 2017

(54) EPITOPE OF IP-10 AND ANTIBODY TO SAME

(71) Applicant: SNU R&DB FOUNDATION, Seoul (KR)

(72) Inventor: Yeong Wook Song, Seoul (KR)

(73) Assignee: SNU R&DB FOUNDATION, Seoul (KR)

(*) Notice: Subject to any disclaimer, the term of this patent is extended or adjusted under 35 U.S.C. 154(b) by 0 days.

(21) Appl. No.: 14/428,301

(22) PCT Filed: Sep. 17, 2013

(86) PCT No.: PCT/KR2013/008447
§ 371 (c)(1),
(2) Date: Mar. 13, 2015

(87) PCT Pub. No.: WO2014/042493
PCT Pub. Date: Mar. 20, 2014

(65) Prior Publication Data
US 2015/0266951 A1 Sep. 24, 2015

(30) Foreign Application Priority Data
Sep. 17, 2012 (KR) ........................ 10-2012-0102739

(51) Int. Cl.
*C07K 16/24* (2006.01)
*C07K 14/52* (2006.01)
*C12P 21/08* (2006.01)
*C07H 21/04* (2006.01)

(52) U.S. Cl.
CPC ............ *C07K 16/24* (2013.01); *C07K 14/522* (2013.01); *C07K 2317/34* (2013.01); *C07K 2317/565* (2013.01); *C07K 2317/76* (2013.01)

(58) Field of Classification Search
None
See application file for complete search history.

(56) References Cited

PUBLICATIONS

Luster et al "γ-Interferon transcriptionally regulates an early-response gene containing homology to platelet proteins", Department of Cellular Physiology and Immunology, Rockefeller University; pp. 672-676 Nature vol. 315 Jun. 20, 1985, New York, New York.
Luster et al "Interferon-inducible gene maps to a chromosomal band associated with a (4;11) translocation in acute leukemia cells" Proc. Nati. Acad. Sci. USA vol. 84, pp. 2868-2871, May 1987.
McTigue et al "Selective Chemokine mRNA Accumulation in the Rat Spinal Cord After Contusion Injury"; Journal of Neuroscience Research 53:368-376 (1998).
Narumi et al "Serum Levels of IFN-Inducible Protein-10 Relating to the Activity of Systemic Lupus Erythematosus", Cytokine, vol. 12. No. 10 (Oct.), 2000: pp. 1561-1565.
Narumi et al "Expression of IFN-Inducible Protein-1 0 in Chronic Hepatitis" The American Association of Immunologists, pp. 5536-5544, 1997.
Neville et al "The Immunobiology of Interferon-gamma Inducible Protein 10 kD (IP-10): a Novel, Pleiotropic Member of the C-X-C Chemokine Superfamily" Cytokirie & Growth Factor Reviews, vol. 8 No. 3, pp. 207-219 1997.
Padovan et al "IFN-a2a induces IP-10/CXCL10 and MIG/CXCL9 production in monocyte-derived dendritic cells and enhances their capacity to attract and stimulate CD8 effector T cells" pp, 669-676; Journal of Leukocyte Biology vol. 71, Apr. 2002.
Patel et al "CXCR3 and CCR5 Ligands in Rheumatoid Arthritis Synovium" Clinical Immunology, vol. 98, No. 1, Jan., pp. 39-45, 2001.
Uguccioni et al "Increased Expression of IP-10, IL-8, MCP-1, and MCP-3 in Ulcerative Colitis", pp. 331-336 American Journal of Pathology. vol. 155, No. 2, Aug. 1999.
Zhang et al, "Donor T Cell Activation Initiates Small Bowel Allograft Rejection Through an IFN-γ-Inducible Protein-10-Dependent Mechanism" The Journal of Immunology 2002; 168:3205-3212; Bethesda, MD.

*Primary Examiner* — Christine J Saoud
*Assistant Examiner* — Jegatheesan Seharaseyon
(74) *Attorney, Agent, or Firm* — Vorys, Sater, Seymour and Pease LLP; Mih Suhn Koh

(57) ABSTRACT

The present invention relates to a novel epitope of IP-10 (IFN-γ-inducible protein 10), to an antibody to the epitope or an antigen-binding fragment thereof, to a composition comprising the epitope as an active ingredient for inducing an antibody to IP-10, and to a pharmaceutical composition comprising the antibody or the antigen-binding fragment thereof for preventing or treating diseases relating to IP-10. The anti-IP-10 antibody of the present invention can be effectively used in preventing or treating various diseases relating to IP-10 such as multiple sclerosis, rheumatoid arthritis and systemic lupus erythematosus.

6 Claims, 14 Drawing Sheets

FIG. 5
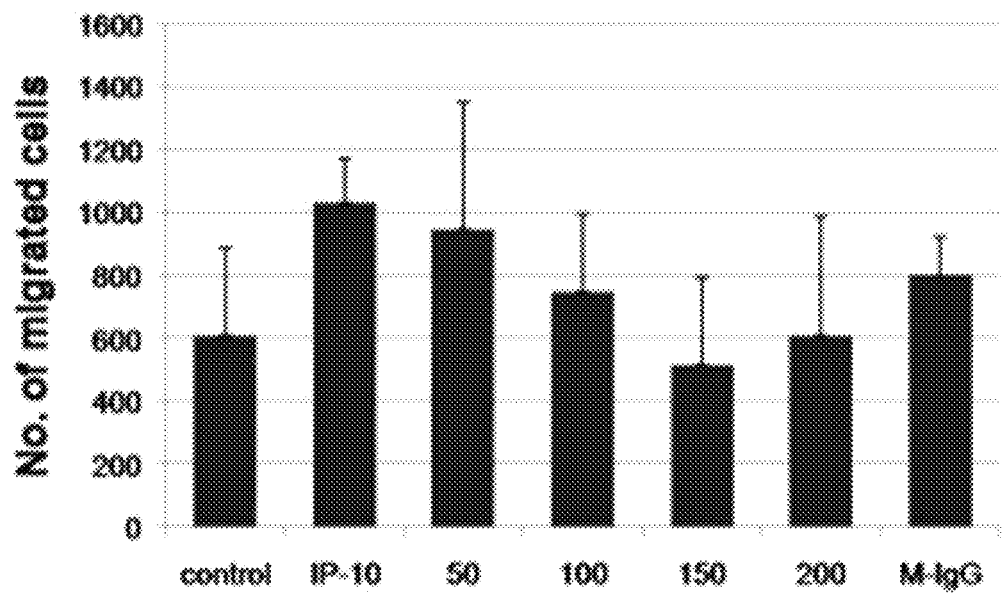
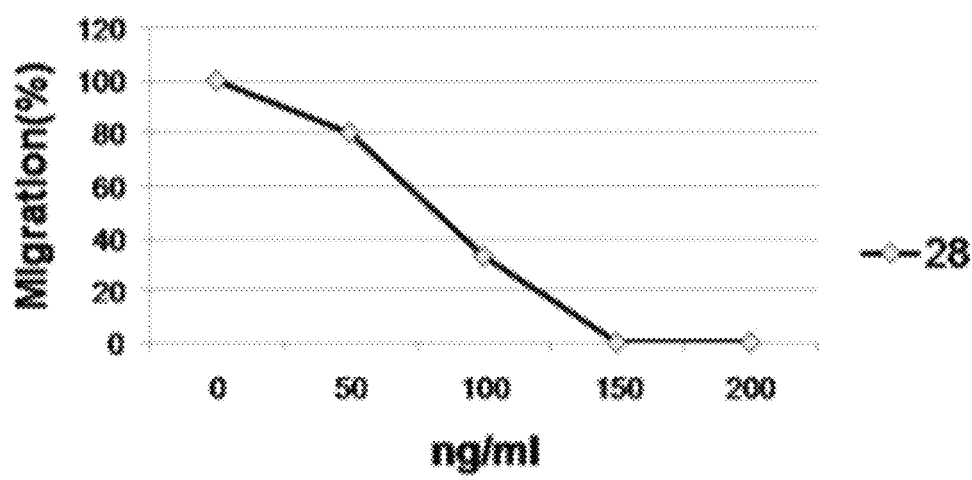

FIG. 10
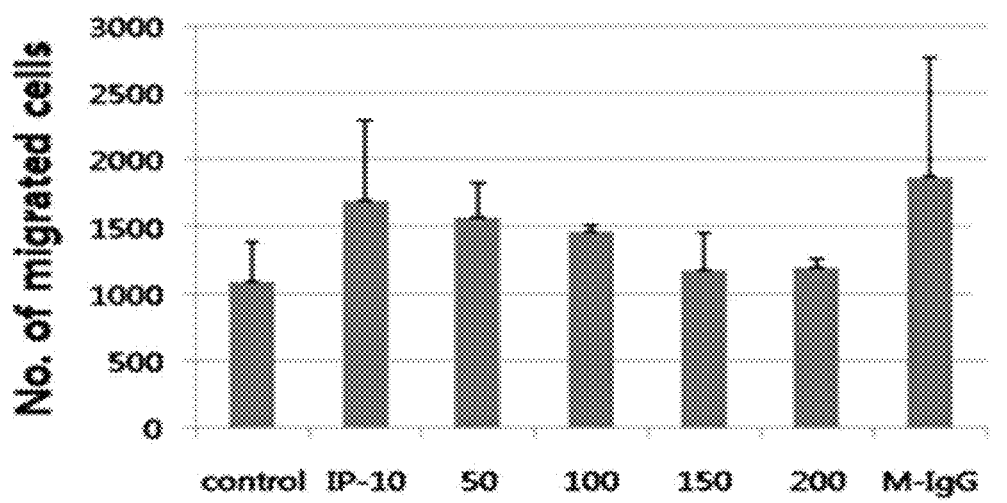
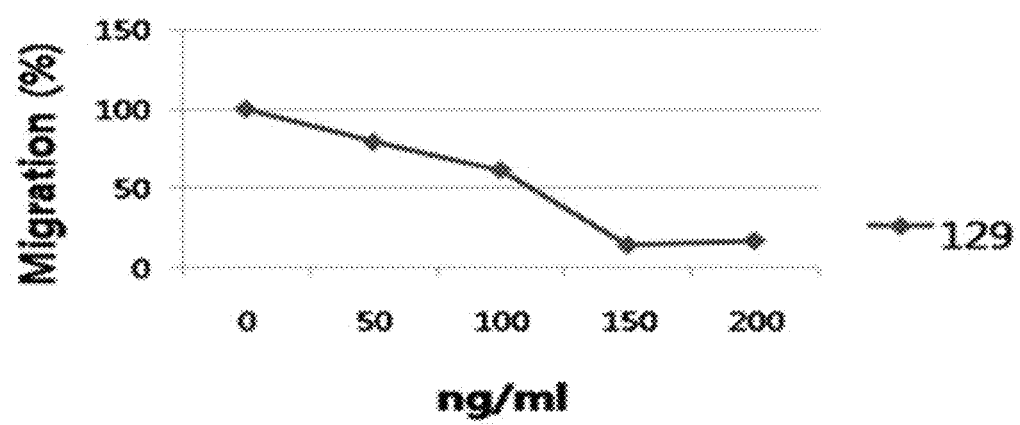

28

M : Marker
Lane1 : IP10 recombinant protein
Lane2 : IP10 Epitope 1 (A01-A40)
Lane3 : IP10 Epitope 2 (A21-A60)
Lane4 : IP10 Epitope 3 (A41-A60)
Lane5 : IP10 Epitope 4 (A61-A98)
Lane6 : GST (negative control)

FIG. 13

```
          1                                                                    50
H25G    MGWTWIFILI  LSVTTGVHSE  VQLQQSGPEL  EKPGASVKIS  CKASGYSFTS
H28G    MELGLNWVFL  VTLLNGIQCE  VKLVESGGGL  VQPGGSLRLS  CAISGFIFTD
H77G    MGWVWTLPFL  MAAAQSIQAQ  IQLVHSGPEL  KKPGETVKIS  CKASGYIFTD
H88G    MELGVSWVFL  VLVLKGVQCE  VMLVESGGGL  VRPGGSLKLS  CTVSGFIFSS
H112G   MGRLTSSFLL  LIVPAYVLSQ  VTLKESGPGI  LKPSQTLSLT  CSFSGFSLST
H116M   MEWTWVILFL  LSITAGVHCQ  VQLQQSGPEL  VKPGASVKIS  CKASGYAFSS
H129G   MAVLVLFFCL  VTFPSCVLSQ  VQLKQSGPGL  VQPSQSLSIT  CTVSGFSLTS

51 CDR1                      CDR2                             100
H25G    ..YNMNWVKQ  SNGKSLEWIG  NIDPYYGG..  TSYNQKFKGK  AILTVDKSSS
H28G    ..YYMSWVRQ  PPGKALEWLG  FIRNKANGYT  TEYSASVKGR  FTISRDNSQS
H77G    ..YSMHWVRQ  APGKGLKWMG  WINTETGE..  PTYADDFKGR  FAFSLETSAS
H88G    ..YAMSWVRQ  TPEKRLEWVA  SITS..GGSY  TSYPDNVKGR  LTISRDNDRN
H112G   SGMGVGWIRQ  PSGKGLEWLA  HIWWDDD...  KFYNPSLKSQ  LTISKDTSRN
H116M   ..SWMNWVKQ  RPGQGLEWIG  RIYPGDGD..  TNYNGKFKGK  ATLIADKSSS
H129G   ..YGVHWVRQ  SPGKGLEWLG  VIWSGGS...  TDYNAAFISR  LSISKDNSKS

101                     CDR3                                  150
H25G    TAYMQLKSLT  SEDSAVYYCA  REGIAW....  ....FAYWGQ  GTLV.......
H28G    ILYLQMNTLR  AEDSATYYCA  RDPTIG....  TVLCYGLLGS  RNLSHRLLRE
H77G    TAYLQINNLK  NEDTATYFCA  RMYDYS....  ..YYFDYWGQ  GTTLTVSSAK
H88G    TLDLQMSSLR  SEDTAMYFCT  RHSPV.....  IASWFAYWGQ  GTLVHC....
H112G   QVFLKITSVD  TADTATYYCA  RRAFSS....  .SANFAYWGP  RDSGKLSLKA
H116M   TAYMQLSSLT  SVDSAVYFCA  RIGNYYGSSY  LYWYFDVWGA  GTTVTVS...
H129G   QVFFKDNSLQ  ANDTAIYYCA  RSWGAM....  .D....YWGQ  GTSVTVSES 151         165
H25G    ..........  .....
H28G    SVLPIRLSPG  PWKLG
H77G    ..........  .....
H88G    ..........  .....
H112G   KNKPP.....  .....
H116M   ..........  .....
H129G   QS........  .....
```

H25G - SEQ ID NO: 93

H28G - SEQ ID NO: 95

H77G - SEQ ID NO: 97

H88G - SEQ ID NO: 99

H112G - SEQ ID NO: 101

H116G - SEQ ID NO: 103

H129G - SEQ ID NO: 105

FIG. 14

```
            1                                                          50
   L25k   ...MELGLSW VFLVTLLNGI QCEVKLVESG GGL.VQPGGS LRLSCATSGF
   L28k   MDFQVQIISF LLISASVIMS RGQIVLTQSP AIMSASPGEK VTISCSASSS
   L77k   MSVLTQVLGL LLLWLTD..A RCDIQMTQSP ASLSVSVGET VTITCRASEN
   L88k   .MKLPVRLLV LMFWIPA..S SSDVLMTQTP LSLPVSLGDQ ASISCRSSQS
   L112k  MVSSAQFLGL LLLCFQG..T RCDIQMTQTT SSLSASLGDR VTISCRASQD
   L116k  MRQSIQFLGL LLFWLHG..A QCDIQMTQSP SSLSASLGGK VTITCKASQD
   L129k  .....MVLMS LLFWVSG..T CGDIVMTQSP SSLSVSAGEK VTMSCKSSQS

CDR1                         CDR2
           51                                                         100
   L25k   TFT....DYY MSWVRQPPGK ALEWLGFIRN KANGYTTEYS ASVKGRFTIS
   L28k   V.......SY MYYQQKPGS SPKPWIY... ....RTSNLA SGVPARF..S
   L77k   I......YSN LAWYQQKQGK SPQLLVY... ....AATNLA DGVPSRF..S
   L88k   IVHS.NGNTY LEWYLQKPGQ SPKLLIY... ....KVSNRF SGVPDRF..S
   L112k  I......SNY LAWYQQKPDG TVKLLIY... ....YTSRLH SGVPSRF..S
   L116k  I......DKY IAWYQHRPGK GPSLLIH... ....YTSTLQ SGIPSRF..S
   L129k  LLNSGNQKNY LAWYQQKPGQ PPKLLIY... ....GASTRE SGVPDRF..T

101                      CDR3                            149
   L25k   RDNSQSILYL QMNTLRAEDS ATYYCARDPT IGTVLCYGLL GSRNLS...
   L28k   GSGSGTSYSL TISSMEAEDA ATYYCQQYHS YPFTFGSGTK WK.......
   L77k   GSGSGTQYSL KINSLQSEDF GSYYCQHFWG TPYTFGGGTK LEIKRADAA
   L88k   GSGSGTDFTL KISRVEAEDM GVYYCFQGSH VPFTFGSGTK LEIKRADAA
   L112k  GSGSGTDYSL TISNLEQEDI ATYFCQQGNT IRSRSVLGPS WS.......
   L116k  GSGSKNYSF SISNLEPEDI ATYYCLQYDN LLLTFGAGTK LELKRADA.
   L129k  GSGSGTDFTL TISSVQAEDL AVYYCQNDHS YPLTFGAGTK LELKRADAA
```

L25G - SEQ ID NO: 94

L28G - SEQ ID NO: 96

L77G - SEQ ID NO: 98

L88G - SEQ ID NO: 100

L112G - SEQ ID NO: 102

L116G - SEQ ID NO: 104

L129G - SEQ ID NO: 106

EPITOPE OF IP-10 AND ANTIBODY TO SAME

CROSS-REFERENCE TO RELATED APPLICATIONS

The present application is a national stage application of International Patent Application No. PCT/KR2013/008447, filed Sep. 17, 2013, and claims the benefit of Korean Patent Application No. 2012-0102739, filed Sep. 17, 2012 in the Korean Intellectual Property Office, the disclosure of which are incorporated herein.

BACKGROUND OF INVENTION

Field of the Invention

The present disclosure relates to IP-10 (IFN-γ-inducible protein 10) epitopes, antibodies to the same and antigen-binding fragments thereof, and compositions for inducing IP-10 antibody comprising the epitope and methods for treating IP-10 related disease comprising the antibody and the antigen-binding fragment thereof.

Description of the Related Art

Interferon-γ-inducible protein 10 (IP-10) is a 10 kDa chemokine which is identified based on its expression in cells treated with IFN-γ (Luster, A. D. et al. Nature 315: 672-676 (1985)). IP-10 shows a homology to a platelet factor 4 and beta thromboglobulin, and to proteins having a mitogenic activity such as a connective tissue activating peptide III (Luster, A. D. et al. Proc. Natl. Acad. Sci. USA 84: 2868-2871 (1987)). IP-10 is secreted from a variety of cells such as endothelial cells, monocytes, fibroblasts and keratinocyte in response to IFN-γ (Padovan, E. et al., J Leukoc. Biol. 71: 669-676 (2002)). For immunobiological characteristics of IP-10, Neville, L. F et al., *Cytokine Growth Factor Rev.* 8: 207-219 (1997) may be referred.

IP-10 or its receptor CXCR3 has also been found to be associated with numerous disorders such as various inflammatory and autoimmune diseases including multiple sclerosis (Neville, L. F et al., *Cytokine Growth Factor Rev.* 8: 207-219 (1997)), rheumatoid arthritis (Patel, D. D. et al. Clin. Immunol. 98: 39-45 (2001)), ulcerative colitis (Uguccioni, M. et al. Am. J. Pathol. 155: 331-336 (1999)), hepatitis (Narumi, S. et al. J. Immunol. 158: 5536-5544 (1997)), spinal cord injury (McTigue, D. M. et al. J. Neurosci. Res. 53: 368-376 (1998)), systemic lupus erythematosus (Narumi, S. et al. Cytokine 12: 1561-1565 (2000)), graft rejection (Zhang, Z. et al. J. Immunol. 168: 3205-3212 (2002)) and Sjogren's syndrome (Sjogren's syndrome; Ogawa, N. et al. Arthritis Rheum. 46: 2730-2741 (2002)). Therefore such diseases as described above may be cured or prevented by suppressing the activity of IP-10.

Numerous scientific papers and patent documents are referenced herein throughout the disclosure, which are incorporated herein by reference in its entirety to describe the level of the related art and the present invention more clearly.

SUMMARY OF THE INVENTION

The present inventors endeavored to find epitopes for the anti-IP-10 (IFN-γ-inducible protein 10) monoclonal antibody. As a result, the present inventors found that the anti-IP-10 monoclonal antibody specifically recognizes an amino acid sequence as set forth in SEQ ID NO: 5 and an amino acid sequence composed of $1^{st}$ to $20^{th}$ amino acids of SEQ ID NO:5.

Thus, the present disclosure is to provide novel epitopes for anti-IP-10 antibody.

Other object of the present disclosure is to provide a nucleic acid molecule encoding the epitopes of the present disclosure.

Still other object of the present disclosure is to provide a recombinant vector comprising the nucleic acid molecule of the present disclosure.

Still other object of the present disclosure is to provide a cell transformed with the recombinant vector of the present disclosure.

Still other object of the present disclosure is to provide an antibody or antigen-binding fragments thereof.

Still other object of the present disclosure is to provide a nucleic acid molecule encoding the heavy chain variable region of the antibody or antigen-binding fragments thereof of the present disclosure.

Still other object of the present disclosure is to provide a nucleic acid molecule encoding the light chain variable region of the antibody or antigen-binding fragments thereof of the present disclosure.

Still other object of the present disclosure is to provide a composition for inducing antibody against IP-10 comprising the present epitopes as an active ingredient.

Still other object of the present disclosure is to provide a pharmaceutical composition for treating or preventing IP-10 related disease comprising the antibody or antigen-binding fragments thereof of the present disclosure.

The foregoing summary is illustrative only and is not intended to be in any way limiting. Additional aspects and/or advantages of the invention will be set forth in part in the description which follows and, in part, will be obvious from the description, or may be learned by practice of the invention.

Advantageous Effects

The present disclosure is characterized as below and also its advantageous effects are summarized as below.

(a) The present disclosure provides novel epitopes for a human IP-10 antibody.
(b) The present disclosure provides an antibody to the present epitope and antigen-binding fragment thereof.
(c) The present anti-IP-10 antibody can be effectively used in preventing or treating various diseases relating to IP-10 such as multiple sclerosis, rheumatoid arthritis and systemic lupus erythematosus.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 5 is the result of a cell migration assay of anti-IP-10 monoclonal antibody #28.

FIG. 10 is the result of a cell migration assay of anti-IP-10 monoclonal antibody #129.

FIG. 13 shows the result of a sequence comparison of a heavy chain variable region of anti-IP-10 monoclonal antibody clone #25, 28, 77, 88, 112, 116 and 129, which are represented by SEQ ID NOs: 93, 95, 97, 99, 101, 103 and 105, respectively.

FIG. 14 shows a sequence comparison result of a light chain variable region of anti-IP-10 monoclonal antibody clone #25, 28, 77, 88, 112, 116 and 129, which are represented by SEQ ID NOs: 94, 96, 98, 100, 102, 104 and 106, respectively.

DETAILED DESCRIPTION OF THE EMBODIMENTS

Figure 1:
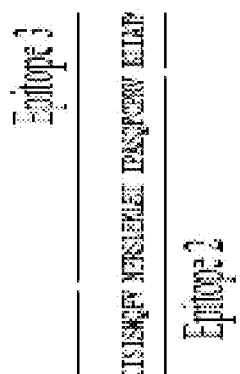
FIG. 1 shows four segments of IP-10 protein identified as Epitope 1 to 4 in which the IP-10 protein is represented by the amino acid sequence of SEQ ID NO: 1, and the amino acid sequence for each of the segments is represented by SEQ ID NOs: 2 to 5, respectively.

In one aspect of the present disclosure, the present disclosure is related to epitopes of IP-10 (IFN-γ-inducible protein 10) which are provided by an amino acid sequence as set forth in SEQ ID NO: 5 and an amino acid sequence composed of $1^{st}$ to $20^{th}$ amino acids of SEQ ID NO:5, which is represented by SEQ ID NO: 6.

In other aspect, the present disclosure provides an antibody to the epitopes of the present disclosure and antigen-binding fragment thereof.

The present inventors endeavored to find epitopes for the anti-IP-10 (IFN-γ-inducible protein 10) monoclonal antibody. As a result, the present inventors found that the anti-IP-10 monoclonal antibody specifically recognizes an amino acid sequence as set forth in SEQ ID NO: 5 and an amino acid sequence composed of $1^{st}$ to $20^{th}$ amino acids of SEQ ID NO:5.

The term "epitope" as used herein refers to an amino acid residue(s) which is recognized by major histocompatibility complex (MHC) and/or T cell receptor proteins in a T cell context, or a set of amino acid residues involved in the recognition by a particular antibody. In the present disclosure epitopes and peptides are interchangeably used. Also encompassed in the present disclosure are isolated or purified proteins or peptides which are larger than and comprising the present epitopes.

As evident from the EXAMPLEs below, anti-IP-10 monoclonal antibody of the present disclosure have a specific binding affinity to an amino acid sequence as set forth in SEQ ID NO: 5 and an amino acid sequence composed of $1^{st}$ to $20^{th}$ amino acids of SEQ ID NO:5 as set forth in SEQ ID NO: 6.

The term "antibody to an epitope of IP-10" refers to proteins that have a specific binding activity an amino acid sequence as set forth in SEQ ID NO: 5 and an amino acid sequence composed of $1^{st}$ to $20^{th}$ amino acids of SEQ ID NO:5.

The antibody of the present disclosure encompasses a whole antibody as well as its antigen-binding fragments (antibody fragment). A whole antibody includes two full length light chain and two full length heavy chains where each light chain is linked to the heavy chain by disulfide bonds. The heavy chain constant regions is divided into isotypes of γ, μ, α, δ and ε types, which are further subtyped into γ1, γ2, γ3, γ4, α1 and α2. The light chain constant region is divided into κ and λ types.

The antigen-binding fragments (antibody fragment) refers to a fragment having an antigen binding activity and includes Fab, F(ab'), F(ab')2 and Fv. Fab is composed of variable regions of a light and a heavy chain and a constant region of a light chain and first constant region (CH1) of a heavy chain thus having one antigen binding region. Fab' is different from Fabs in that it comprises a hinge region which comprises at least one cysteine residue at C-terminal of the CH1 domain of a heavy chain. F(ab')2 is produced by a disulfide bond formation between cysteine residues in the hinge region of Fab'. Fv is an antibody fragment composed only of variable regions of a heavy and a light chain, which may be produced by a recombinant technology as disclosed in WO 88/10649, WO 88/106630, WO 88/07085, WO 88/07086 and WO 88/09344. In Fv (two-chain Fv), variable regions of a light and heavy chain are linked by a non-covalent bond, and in a single chain Fv, variable regions of a light and heavy chain are linked by a covalent bond through a peptide linker or it may form a dimer structure like a two chain FV through a direct linkage at the C-terminal. These antibody fragments are obtained through a proteinase treatment (for example, a whole antibody may be treated with a papain to obtain Fab fragments) or with a pepsin to obtain F(ab')2 fragment or preferably obtained through a recombinant DNA technology.

In the present disclosure, the heavy chain constant region is anyone of isotypes of γ, μ, α, δ and ε types, and the light chain constant region is anyone of κ and λ types.

The term "heavy chain" as used herein refers to a full length chain comprising three constant regions CH1, CH2 and CH3 and one variable region VH comprising an amino acid sequence which is sufficient for conferring specificity to an antigen as well fragments thereof. Also The term "light chain" as used herein refers to refers to a full length chain comprising one constant region CL and one variable region VL comprising an amino acid sequence which is sufficient for conferring specificity to an antigen as well fragments thereof.

In one preferred embodiment, the present antibody comprises anyone of the following heavy chain variable region:
(i) CDR H1 of SEQ ID NO: 51, CDR H2 of SEQ ID NO: 52 and CDR H3 of SEQ ID NO: 53;
(ii) CDR H1 of SEQ ID NO: 54, CDR H2 of SEQ ID NO: 55 and CDR H3 of SEQ ID NO: 56;
(iii) CDR H1 of SEQ ID NO: 57, CDR H2 of SEQ ID NO: 58 and CDR H3 of SEQ ID NO: 59;
(iv) CDR H1 of SEQ ID NO: 60, CDR H2 of SEQ ID NO: 61 and CDR H3 of SEQ ID NO: 62;
(v) CDR H1 of SEQ ID NO: 63, CDR H2 of SEQ ID NO: 64 and CDR H3 of SEQ ID NO: 65;

(vi) CDR H1 of SEQ ID NO: 66, CDR H2 of SEQ ID NO: 67 and CDR H3 of SEQ ID NO: 68; or (vii) CDR H1 of SEQ ID NO: 69, CDR H2 of SEQ ID NO: 70 and CDR H3 of SEQ ID NO: 71.

In one preferred embodiment, the present antibody comprises anyone of the following light chain variable region:

(i) CDR L1 of SEQ ID NO: 72, CDR L2 of SEQ ID NO: 73 and CDR L3 of SEQ ID NO: 74;

(ii) CDR L1 of SEQ ID NO: 75, CDR L2 of SEQ ID NO: 76 and CDR L3 of SEQ ID NO: 77;

(iii) CDR L1 of SEQ ID NO: 78, CDR L2 of SEQ ID NO: 79 and CDR L3 of SEQ ID NO: 80;

(iv) CDR L1 of SEQ ID NO: 81, CDR L2 of SEQ ID NO: 82 and CDR L3 of SEQ ID NO: 83;

(v) CDR L1 of SEQ ID NO: 84, CDR L2 of SEQ ID NO: 85 and CDR L3 of SEQ ID NO: 86;

(vi) CDR L1 of SEQ ID NO: 87, CDR L2 of SEQ ID NO: 88 and CDR L3 of SEQ ID NO: 89; or (vii) CDR L1 of SEQ ID NO: 90, CDR L2 of SEQ ID NO: 91 and CDR L3 of SEQ ID NO: 92.

In a more preferred embodiment, the present antibody comprises the following heavy chain variable region and light chain variable region.

(i) a heavy chain variable region comprising CDR (complementarity determining region) H1 of SEQ ID NO: 51, CDRH2 of SEQ ID NO: 52 and CDRH3 of SEQ ID NO: 53; and a light chain variable region comprising CDRL1 of SEQ ID NO: 72, CDRL2 of SEQ ID NO: 73 and CDRL3 of SEQ ID NO: 74;

(ii) a heavy chain variable region comprising CDR (complementarity determining region) H1 of SEQ ID NO: 54, CDRH2 of SEQ ID NO: 55 and CDRH3 of SEQ ID NO: 56; and a light chain variable region comprising CDRL1 of SEQ ID NO: 75, CDRL2 of SEQ ID NO: 76 and CDRL3 of SEQ ID NO: 77 (H28G monoclonal antibody);

(iii) a heavy chain variable region comprising CDR (complementarity determining region) H1 of SEQ ID NO: 57, CDRH2 of SEQ ID NO: 58 and CDRH3 of SEQ ID NO: 59; and a light chain variable region comprising CDRL1 of SEQ ID NO: 78, CDRL2 of SEQ ID NO: 79 and CDRL3 of SEQ ID NO: 80 (H77G monoclonal antibody);

(iv) a heavy chain variable region comprising CDR (complementarity determining region) H1 of SEQ ID NO: 60, CDRH2 of SEQ ID NO: 61 and CDRH3 of SEQ ID NO: 62; and a light chain variable region comprising CDRL1 of SEQ ID NO: 81, CDRL2 of SEQ ID NO: 82 and CDRL3 of SEQ ID NO: 83 (H88G monoclonal antibody);

(v) a heavy chain variable region comprising CDR (complementarity determining region) H1 of SEQ ID NO: 63, CDRH2 of SEQ ID NO: 64 and CDRH3 of SEQ ID NO: 65; and a light chain variable region comprising CDRL1 of SEQ ID NO: 84, CDRL2 of SEQ ID NO: 85 and CDRL3 of SEQ ID NO: 86;

(vi) a heavy chain variable region comprising CDR (complementarity determining region) H1 of SEQ ID NO: 66, CDRH2 of SEQ ID NO: 67 and CDRH3 of SEQ ID NO: 68; and a light chain variable region comprising CDRL1 of SEQ ID NO: 87, CDRL2 of SEQ ID NO: 88 and CDRL3 of SEQ ID NO: 89; or (vii) a heavy chain variable region comprising CDR (complementarity determining region) H1 of SEQ ID NO: 69, CDRH2 of SEQ ID NO: 70 and CDRH3 of SEQ ID NO: 71; and a light chain variable region comprising CDRL1 of SEQ ID NO: 90, CDRL2 of SEQ ID NO: 91 and CDRL3 of SEQ ID NO: 92.

According to a more preferred embodiment of the present disclosure, the present antibody comprises: (i) a heavy chain variable region of SEQ ID NO: 93 and a light chain variable region of SEQ ID NO: 94 (clone #25 monoclonal antibody); (ii) a heavy chain variable region of SEQ ID NO: 95 and a light chain variable region of SEQ ID NO: 96 (clone #28 monoclonal antibody); (iii) a heavy chain variable region of SEQ ID NO: 97 and a light chain variable region of SEQ ID NO: 98 (clone #77 monoclonal antibody); (iv) a heavy chain variable region of SEQ ID NO: 99 and a light chain variable region of SEQ ID NO: 100 (clone #88 monoclonal antibody); (v) a heavy chain variable region of SEQ ID NO: 101 and a light chain variable region of SEQ ID NO: 102 (clone #112 monoclonal antibody); (vi) a heavy chain variable region of SEQ ID NO: 103 and a light chain variable region of SEQ ID NO: 104 (clone #116 monoclonal antibody); or (vii) a heavy chain variable region of SEQ ID NO: 105 and a light chain variable region of SEQ ID NO: 106 (clone #129 monoclonal antibody).

Encompassed in the present antibody is monoclonal antibody, polyclonal antibody, multispecific antibody, humanized antibody, human antibody, chimeric antibody, a single chain Fvs(scFV), a single chain antibody, Fab fragment, F(ab') fragment, disulfide-linked Fvs(sdFV) and anti-idiotype (anti-Id) antibody and epitope-binding fragment thereof, but is not limited thereto.

The present epitope, antibody or fragment thereof is represented by the sequences as disclosed herein and also encompassed are their equivalent. For example, to improve the binding affinity and/or other the biological characteristics of antibodies, the antibodies may be modified at the amino acid sequences. These modifications for example include a deletion, insertion and/or substitution in one or more of the amino acid residues. These modifications in the amino acids are usually performed based on the relative similarity such as hydrophobicity, hydrophilicity, charges and sizes between the side chains of the amino acid to be modified and the substituent. For example, side chains of arginine, lysine and histidine are positively charged; side chains of alanine, glycine and serine are similar in size; and side chain of phenylalanine, tryptophan and tyrosine are similar in shape. Therefore, arginine, lysine and histidine; alanine, glycine and serine; and phenylalanine, tryptophan and tyrosine are considered to be equivalent to each other within each group.

In introducing modifications, that which may be considered is a hydrophobicity index. Each amino acid is given an index according to their hydrophobicity and charges as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In assigning an interactive biological function, hydrobicity scale of amino acids are very important. It is known in the art that amino acids similar in hydrophobic index are necessary to obtain a similar biological activity. When mutations are introduced in consideration of a hydrophobic index, the differences in the indices preferably within ±2, more preferably within ±1, most preferably within ±0.5 are used for a substitution.

Also known in the art is that substitutions between amino acids with similar hydrophilicity value result in the protein equivalent in biological activity. U.S. Pat. No. 4,554,101 discloses a hydrophilicity value for each amino acid as follows: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Amino acid substitutions that do not alter the overall activity of a protein are known in the art (H. Neurath, R. L. Hill, The Proteins, Academic Press, New York, 1979). The most common substitutions are Ala to Ser, Val to Ile, Asp to Glu, Thr to Ser, Ala to Gly, Ala to Thr, Ser to Asn, Ala to Val, Ser to Gly, Thr to Phe, Ala to Pro, Lys to Arg, Asp to Asn, Leu to Ile, Leu to Val, Ala to Glu and Asp to Gly substitutions.

In consideration of the modifications as described above, it is interpreted that the present epitopes, antibodies, or nucleic acid molecules encoding the same also encompass the ones having a substantial similarity to the sequences as disclosed herein. The substantial similarity means at least 61% homology, more preferably 70% homology, further more preferably 80% homology, most preferably 90% homology in when the present sequences are aligned with any other sequences and the alignment is analyzed by a conventional algorithm. Methods for alignment for sequence comparison are known in the art. For various methods for alignment and algorithm, Smith and Waterman, Adv. Appl. Math. (1981) 2:482; Needleman and Wunsch, J. Mol. Bio. (1970) 48:443; Pearson and Lipman, Methods in Mol. Biol. (1988) 24: 307-31; Higgins and Sharp, Gene (1988) 73:237-44; Higgins and Sharp, CABIOS (1989) 5:151-3; Corpet et al., Nuc. Acids Res. (1988) 16:10881-90; Huang et al., Comp. Appl. BioSci. (1992) 8:155-65 and Pearson et al., Meth. Mol. Biol. (1994) 24:307-31 may be referred. NCBI Basic Local Alignment Search Tool (BLAST)(Altschul et al., J. Mol. Biol. (1990) 215:403-10) is accessible at NBCI, which may be used with a sequence analysis program such as blastp, blasm, blastx, tblastn and tblastx on the internet. BLSAT is accessible at www.ncbi.nlm.nih.gov/BLAST/. Methods for comparing sequence homology using BLAST can be found in www.ncbi.nlm.nih.gov/BLAST/blast_help.html.

In other aspect, the present disclosure provides a nucleic acid molecule encoding the present epitopes.

In still other aspect, the present disclosure provides a nucleic acid molecule encoding the antibody or the antigen-binding fragments of heavy chain variable region or light chain variable region of the present antibody.

The term "nucleic acid molecules" as used herein refers to a DNA (gDNA and cDNA) and RNA. Also included are nucleic acids which comprises a natural nucleotide as a building block as well as its analogues in which sugar moiety or bases are modified (Scheit, Nucleotide Analogs, John Wiley, New York (1980); Uhlman and Peyman, Chemical Reviews, (1990) 90:543-584). The nucleic acid sequences may be modified. Such modifications include an addition, a deletion of at least one of nucleotides, or a conservative and non-conservative substitution.

In one preferred embodiment of the present disclosure, the nucleic acid molecule encoding the present heavy chain variable region is represented by SEQ ID NOs: 107, 108, 109, 110, 111, 112 or 113, and the nucleic acid molecule encoding the present light chain variable region is represented by SEQ ID NOs: 114, 115, 116, 117, 118, 119 or 120.

In one preferred embodiment of the present disclosure, the nucleic acid molecule encoding the variable region of the present antibody may be a part of a nucleic acid molecule encoding the entire heavy chain or the entire light chain.

It is interpreted that the present nucleic acid molecule also comprises ones that is substantially identical to the sequences as disclosed herein. The substantially identical or substantial identity means at least 80% homology, more preferably at least 90% homology, most preferably at least 95% homology in sequences when the present nucleotide sequences are aligned with any other sequences and the alignments are analyzed using algorithms conventionally used in the art.

According to other embodiment of the present disclosure, the present disclosure provides a vector comprising a nucleic acid molecule encoding the present epitope.

According to other embodiment of the present disclosure, the present disclosure a recombinant vector comprising: (a) a nucleic acid molecule encoding the present heavy chain variable region; and (b) a nucleic acid molecule encoding the present light chain variable region.

The term "vector" as used herein is a means to express a desired gene in a host cell and includes vectors such as a plasmid vector; a cosmid vector; and a bacteriophage vector, an adenovirus vector, a retro virus vector and an adeno-associated vector.

In one preferred embodiment of the present disclosure, the nucleic acid molecule in the vector is operatively linked to a promoter.

The term "operatively linked" means a functional linkage between a regulatory sequence for nucleic acid expression (example: a promoter, a signal sequence, or array of positions to which transcriptional factors bind) and other nucleic acid sequences, and by which the regulatory sequences are able to control the transcription and/or translation of the other nucleic acid sequence.

The recombinant vector system can by constructed using various methods known in the art and Sambrook et al., Molecular Cloning, A Laboratory Manual, Cold Spring Harbor Laboratory Press (2001), which is incorporated herein by reference may be referred.

The present vectors may be constructed as a vector for cloning or for expression. Also, the present vectors may be constructed for eukaryotic or prokaryotic cells. For example, when the present vector is an expression vector in a prokaryotic cell, a strong promoter for transcription such as a tac promoter, a lac promoter, a lacUV5 promoter, a lpp promoter, a pLλ promoter, a pRλ promoter, a rac5 promoter, amp promoter, a recA promoter, SP6 promoter, trp promoter and a T7 promoter and the like and a ribosomal binding site for a translational initiation and a transcriptional/translational termination sequence. As a host cell, when *E. coli* such as HB101, BL21, DH5α and the like is used, an operator and promoter for *E. coli* tryptophan biosynthesis (Yanofsky, C., J. Bacteriol., (1984) 158:1018-1024) and a phage λ left promoter (pLλ promoter, Herskowitz, I. and Hagen, D., Ann. Rev. Genet., (1980) 14:399-445) may be used a regulatory sequence. When bacilli are used as host cells, the promoter for a toxin gene from *bacillus thuringiensis* (Appl. Environ. Microbiol. (1998) 64:3932-3938; Mol. Gen. Genet. (1996) 250:734-741) or any promoters which may drive the expression of a gene may be used as a regulatory sequence.

When the present vector is an expression vector in a eukaryotic cell, promoters derived from genomes of mammalian cells (examples: a metallothionein promoter, β-actin promoter, human hemoglobin promoter and human muscle creatinine promoter) or promoters derived from mammalian viruses (examples: an adenovirus late promoter, a vaccinia virus 7.5K promoter, SV40 promoter, cytomegalovirus (CMV) promoter, a tk promoter of HSV, a promoter of mouse mammary tumor virus (MMTV), a LTR promoter of HIV, a promoter of moloney virus, a promoter of Epstein Barr Virus, a promoter of Rous Sarcoma Virus may be use. And the vector includes a polyadenylate sequence as a transcriptional termination sequence.

The present recombinant vector may be fused with additional nucleotide sequences to facilitate the isolation and purification of the polypeptide expressed from the vector. The nucleotide sequences to be fused with the present vector include for example Glutathione S-Transferase (Pharmacia, USA), Maltose Binding Protein (NEB, USA), FLAG (IBI, USA) and 6× His (hexahistidine; Quiagen, USA) and the like. Also when the protein expressed from the present vector is an antibody, the antibody expressed may be isolated using Protein A column and the like and the additional nucleotide sequences may not be needed.

The vector which may be used to express the present antibody may express a heavy and a light chain in one vector or each of a heavy and a light chain in a separate vector, respectively. In the latter case, the two vectors employed are introduced to a host cell by co-transfection and targeted transfection. The co-transformation is a method to introduce into a host cell two vector DNAs each encoding a light and a heavy chain, respectively and select a transfected cell which express both a light and a heavy chain. A targeted transfection is a method to first select a transfected cell which expresses a light (or a heavy chain) chain and then the transfected cell is transfected again with a vector encoding a heavy (or a light chain) chain to select a cell that expresses both a light and a heavy chain.

In other aspect of the present disclosure, the present disclosure provides a cell which is transfected with a recombinant vector harboring the present epitope-coding nucleic acid molecule or antibody (or its antigen-binding fragment)-coding nucleic acid molecule.

Host cells which may be used for the present disclosure any host cells which are known in the art and may be used for a cloning and expression, and include prokaryotic cells such as *Escherichia coli*, *Bacillus* sp. such as *Bacillus subtilis* and *Bacillus thuringiensis*, *Streptomyces* sp., *Pseudomonas* sp. (for example, *Pseudomonas putida*)), *Proteus mirabilis* or *Staphylococcus* sp. (for example, *Staphylococcus carnosus*), but are not limited thereto.

Eukaryotic host cells which are suitable to be used with the present vector include fugi such as *Aspergillus* sp. and yeast such as *Pichia pastoris*, *Saccharomyces cerevisiae*, *Schizosaccharomyces* and *Neurospora crassa* and other lower eukaryotic cells, and a higher eukaryotic cells such as insect-derived cells, and cells derived from plants and mammals. Microorganisms such as *E. coli* may have a high yield but may not be suitable for producing Ig in a intact form but may be used for producing Fab and Fv and the like.

The terms "transformation" and/or "transfection" as used herein refer to any methods to introduce nucleic acid molecules to organisms, cells, tissues or organs which may be performed according to the suitable standard procedures selected from what is known in the art. Such methods include an electroporation, a plasma fusion, $CaPO_4$ precipitation methods, $CaCl_2$ precipitation methods, stirring methods using silicon carbide fibers, a transformation mediated by agro bacteria, a chemical mediated gene transfer such as PEG, dextran sulfate and lipid, and a dry/inhibition-mediated transformation but are not limited thereto.

According to other aspect of the present disclosure, the present disclosure provides a method for preparing the present antibody, antigen-binding fragment thereof which comprises (a) a step of culturing cells which are transformed with anyone of the present vector; and (b) a step of expressing the present antibody, antigen-binding fragment thereof in the cell.

The culturing step of the present methods can be performed using a suitable medium and conditions known in the related art. The person skilled in the art would be able to modify the culture conditions according to the particular cells employed without difficulty. These methods are disclosed in various documents for example such as James M. Lee, Biochemical Engineering, Prentice-Hall International Editions, 138-176). Methods for culturing cells may be divided into a suspension culture and an adherent culture based on the cell growth mode, and into a batch method, a fed-batch method and a continuous method according to the culture mode. The media employed for the culture should be selected to meet the conditions required by the particular cells employed.

The epitopes or the antibodies thus obtained from the cells transformed and cultured as described above may be used without purification, or may be used with purification which may be performed using methods known in the art for example, a dialysis, a salt precipitation and a chromatography method and the like.

According to other aspect of the present disclosure, the present disclosure provides composition for inducing antibody to IP-10 comprising the present polypeptides as an effective ingredient.

According to still other aspect of the present disclosure, the present disclosure provides a pharmaceutical composition for treating or preventing IP-10 related disease comprising (a) a pharmaceutically effective amount of the present antibody or antigen-binding fragments thereof; and (b) a pharmaceutically acceptable carrier.

The present antibody or antigen-binding fragment thereof which is included in the present composition is as described above.

In one preferred embodiment, the present composition for inducing antibody to IP-10 may be used to induce an antibody formation and to prepare antibody to IP-10, which may be achieved by a method comprising a step of inducing an immune reaction in an animal by administering the present composition to the animal; and a step of isolating an antibody that specifically recognize the polypeptide from the serum of the animal.

In one preferred embodiment, the present composition for inducing antibody to IP-10 may be a pharmaceutical composition for treating or preventing IP-10 related disease.

Preferably, the IP-10 related disease is selected from the group consisting of bone disease associated by osteoclast related to RANKL (receptor agonist for NF-κB ligand), multiple sclerosis, ulcerative colitis, hepatitis, systemic lupus erythematosus and Sjogren's syndrome. More preferably, the bone disease is selected from the group consisting of osteoporosis, juvenile osteoporosis, dysostosis, hypercalcemia, hyperparathyroidism, osteomalacia, osteolytic bone disease, osteonecrosis, Paget's disease of bone, bone loss associated with rheumatoid arthritis, osteomyelitis, metastatic bone disease, alveolar bone loss, cancer-related bone loss, age-related loss of bone mass.

The present pharmaceutical composition comprises a pharmaceutically acceptable carrier. The pharmaceutically acceptable carrier which may be used for the present disclosure is a material conventionally employed for preparing medicaments and includes a lactose, a dextrose, a sucrose, a sorbitol, a mannitol, a starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oils but is not limited thereto. The present pharmaceutical composition may additionally include lubricants, moistening agents, sweetening agents, flavoring agents, emulsifiers, suspending agents and preservatives and the like. Suitable agents and pharmaceutically acceptable carriers are disclosed in detail in Remington's Pharmaceutical Sciences (19th ed., 1995).

The present pharmaceutical composition may be administered via a oral or parenteral route. The parenteral administration may include an intravenous injection, a subcutaneous injection, an intramuscular injection, a peritoneal injection, an endothelial administration, a nasal administration, an intrapulmonary administration, and a rectal administration and the like. For the oral administration, the active ingredient in the composition needs to be formulated into a coated dosage form or into a dosage form which can protected the active ingredient from being disintegrated in stomach considering that peptides and proteins are digested in stomach. Or the present composition may be administered via a means by which the active ingredient moves to the target cell of interest.

The amount of administration may vary depending on various factors such as dosage forms, routes of administration, age, body weight, sex, disease states, foods, time of administration, excretion rate and susceptibility and the like. The experts of ordinary skilled in the art would be able to determine and prescribe the amount to be administered, which is effective for treating and preventing disease of interest.

The present pharmaceutical composition may be manufactured by encasing the composition in multi-dose vials or in a dosage form which may be formulated in pharmaceutically acceptable carriers and/or excipients according to the methods which can be easily practiced by the person of ordinary skill in the field to which the present invention pertains. The dosage form may be a solution in a lipid or aqueous medium, suspensions, emulsions and elixirs, suppository forms, granules, powders, tablets or capsules and additionally include dispersion agents and stabilizers, In a further aspect, the present disclosure provides a method for treating or preventing IP-10 related disease selected from the group consisting of osteoporosis, juvenile osteoporosis, dysostosis, hypercalcemia, hyperparathyroidism, osteomalacia, osteolytic bone disease, osteonecrosis, Paget's disease of bone, bone loss associated with rheumatoid arthritis, osteomyelitis, metastatic bone disease, alveolar bone loss, cancer-related bone loss, age-related loss of bone mass by administering to a subject in need thereof an effective amount of the composition according to the present disclosure comprising (a) an antibody and antigen-binding fragment thereof; (b) a pharmaceutically acceptable carriers of the present disclosure.

The methods described above utilize the present composition as described above and thus the description is omitted to avoid the unnecessary complexity of the specification.

The present disclosure is further explained in more detail with reference to the following examples. These examples, however, should not be interpreted as limiting the scope of the present invention in any manner.

EXAMPLES

Material and Methods
Epitope Analysis
IP-10 protein (represented by SEQ ID NO: 1) was divided into 4 segments to determine its epitope recognized by anti IP-10 antibody, Each segment was 40 amino acids long and they are partially overlapped. As shown in FIG. 1, Epitope 1 (epitope 1: SEQ ID NO: 2) consists of $1^{th}$ to $40^{th}$ amino acid, Epitope 2 (epitope 2: SEQ ID NO: 3) from $20^{th}$-$60^{th}$ amino acid, Epitope 3 (epitope 3; SEQ ID NO: SEQ ID NO: 4) from $41^{th}$-$80^{th}$ amino acid, Epitope 4 (epitope 4; SEQ ID NO: 5) from $61^{th}$-$98^{th}$ amino acid.

DNA for each segment was amplified by PCR. Fifty ng of a commercial plasmid encoding IP-10 (catalogue number: MHS1011-74663, BENEBIOSIS, Korea) was used as a template and primers used are shown in the table below. To facilitate the cloning process, primers were designed to contain EcoRI (GATTC) and XhoI (CTCGAG) recognition site on the 5' and 3' ends, respectively.

TABLE 1

| Primer | Sequence | SEQ ID NO |
|---|---|---|
| IP-10-segment 1 sense | GCTAGAATTCATGAATCAAACTGCCA | 7 |
| IP-10-segment 1 anti-sense | GATCCTCGAGAATAGGTTGATTAC | 8 |
| IP-10-segment 2 sense | GCTAGAATTCGGAGTACCTCTCTAG | 9 |
| IP-10-segment 2 anti-sense | ATCCTCGAGAACACGTGGACAAAATTG | 10 |
| IP-10-segment 3 sense | GCTAGAATTCAATCCAAGGTCTTTAG | 11 |
| IP-10-segment 3 anti-sense | ATCCTCGAGCTTCGATTCTGGATTC | 12 |
| IP-10-segment 4 sense | GCTAGAATTCGAGATCATTGCTACAATG | 13 |
| IP-10-segment 4 anti-sense | GATCCTCGAGAGGAGATCTTTAGAG | 14 |

Gel-Elution Method

The PCR products were separated on a 1% agarose gel and JetSorb Gel extraction Kit (GENOMED, USA) was used to extract DNA from the agarose gel. Each band on the gel was excised out under UV. The excised gel was dissolved in 300 µl of A1 buffer and 10 µl of JetSorb suspension for 15 min at 50° C. Then the solution was centrifuged at 10000 rpm for 1 min and the supernatant was removed. Then 300 µl of A1 buffer was added to the pellet. The same procedure was repeated twice. After the washing JetSorb suspension was exposed to air for 40 min and DNA was eluted for 5 min at 50° C. by adding 200 µl of distilled water, which was then centrifuged at 10000 rpm for 1 min and used for cloning.

The purified DNA and PET41 vector (catalogue number: 70556-3, Novagen, Germany) was digested with EcoRI and XhoI, which was then separated on a 1% agarose gel. The DNA fragment was purified from the gel as described above and ligated using T4 ligase.

The ligated products were then transformed into E. coli (catalog number: C66411, Invitrogen, USA), which was then spread on agar plate containing kanamycin. Each of the colonies formed was inoculated in a 2 ml of LB-kanamycin broth and incubated overnight at 37° C. while shaking. The plasmids were purified using QIA prep Spin Miniprep kit (catalog number: 27106, QUIAGEN, UA). The plasmid was confirmed by DNA sequencing and used for E. coli TOP10 (catalog number: C66411, Invitrogen, USA) transformation to obtain a colony containing the plasmid desired.

Production of Recombinant IP-10 Protein

A colony harboring the plasmid pET41-IP10 part/BL21 (DE3) as obtained above was inoculated and incubated overnight at 37° C. while shaking (200 rpm), which was repeated next day. When OD was reached 0.4-0.6 at 600 nm, IPTG (Isopropyl β-D-1-thiogalactopyranoside) was added to the broth at the final concentration of 1 nm to induce the expression of protein for 4 hours, Then the culture was centrifuged for 20 min at 7000 rpm and the pellet was collected.

Western Blot Analysis

E. coli expressing each of the 4 epitopes of recombinant IP-10 was suspended in PBS buffer (137 mM NaCl, 2.7 mM KCl, 10 mM Na2HPO4.2 mM KH2PO4) and the same volume of SDS-gel loading buffer (100 mM Tris-Cl (pH 6.8), 4% SDS, 0.2% bromophenol blue, 20% glycerol, 200 mM DTT) and heated at 100° C. for 5 min. The mixture was then centrifuged at 13,000 rpm for 10 min and the supernatant was separated on 12% SDS-PAGE, and the proteins separated on the gel were transferred to a polyvinylidenfluoride membrane. Western blot was performed using anti-IP-10 antibody and enhanced chemiluminescent reagent.

Cell Migration Assay

To the upper chamber of a transwell of 3 μm in size (trans well, Corning N.Y.), 0.1 ml of Jurkat cell (clone E 6-1, $2.5 \times 10^5$) in a medium without fetal bovine serum was added. To the lower chamber of the transwell, 0.6 ml of medium without FBS and 200 ng/ml of recombinant IP-10 (Peprotech, USA) were added. Then 200 ng/ml of mouse IgG (BD Pharmingen, USA) or 0-200 ng/ml of anti-IP-10 antibody was added to the upper and lower chamber. The upper chamber was put inside of the lower chamber and incubated for 37° C. for 16-18 hours and the content of the chamber was removed. Number of cells migrated was counted using a phase contrast microscopy in 9 different fields, which were confirmed by trypan blue staining. Results are representative of three independent experiments in triplicates Immunoglobulin PCR Analysis To obtain the sequence information of the produced IP-10 antibody protein and DNA, a total RNA was separated from hybridoma cells producing monoclonal antibody for cDNA synthesis, the sequence of which was confirmed by PCR using primers specific for immunoglobulin.

Generation of Hybridoma Cell Line and Production of Anti-IP-10 Antibody

An emulsion of PBS (phosphate-buffered saline) comprising IP-10 antigen and the same volume of complete Freund's adjuvant was administered peritoneally to a female BALB/C mouse of 6-8 weeks. Three to five mice were used and 1 to 100 μg of antigen in a total volume of 200-400 μl was used per mouse. The injection was repeated two weeks after the first injection and then the last injection was given in half the amount of antigen in PBS that was used for the previous injection. Two days after the last booster injection, a blood sample was taken from the tail vein and the serum prepared therefrom was diluted 1:1000 in PBS and subjected to ELISA to determine the titer. The successful immunization was judged based on the absorption reading of at least 0.2 compared to that of a negative control which did not receive the antigen. If the titer was below that value, additional booster injection was given. Two weeks before the hybridoma experimentation, myeloma cells were retrieved from the liquid nitrogen storage and cultured in complete DMEM comprising 10% fetal bovine serum. The state of the cell and contamination was examined under the inverted microscope. When the concentration of cells reached $5 \times 10^5$/ml and the cells were diluted to 1/10-1/20 ratio and the medium was changed every 1.5 to 2 days. One day before the fusion experiment, the concentration of the cells was adjusted to $2 \times 10^5$/ml.

The mouse was sacrificed to harvest the spleen, from which the fat tissue was removed. Then the spleen was placed on a petri dish and perfused with 8 ml of washing medium using a syringe and mashed. The cell suspension was placed in 15 ml of conical tube and allowed to settle for 3 min and the supernatant was transferred to a new tube. In the meantime, cultured myeloma cells were harvested and transferred to a 50 ml conical tune and centrifuged at 200 g for 5 min. To the cell, washing medium was added and the cells were resuspended by repeated pipetting and centrifuged again at 200 g for 5 min and the supernatant was removed. The prepared myeloma cells were resuspended in 10 ml of washing medium and the number of cells was counted. Then myeloma cells and the spleen cells prepared as above was mixed at the concentration of $1 \times 10^7$ cells/ml and $1 \times 10^8$ cells/ml, respectively in a 50 ml tube in a washing medium. Then the mixture was centrifuged at 200 g for 5 min and the supernatant was discarded. Then the cells were incubated in a beaker with 37° C. water for 2 min, after which 1 ml of PEG was added to the tube with a gentle shaking followed by a centrifuge at 100 g for 2 min. Then 5 ml of washing medium was added over 3 min followed by additional 5 ml over 2 min. The medium was then removed by centrifuge at 200 g for 2.5 min and the cells were suspended in 30 ml of HAT and incubated in a CO2 incubator for 30 min with the lid open. Then 100 μl of the cells was added to each well of a 96 well plate with feeder cells from the mouse plated thereon. After 4-5 days, 70 μl of HAT was added. Colonies were formed at 5-7 days after the seeding, and the supernatant was harvested every 2 days to confirm the presence of the antibody by ELISA.

Isolation of Total RNA and cDNA Synthesis

A total RNA was isolated from the hybridoma cell line producing IP-10 monoclonal antibody as prepared above using TRIZOL® (catalog number: 15596, Invitrogen, USA) according to the manufacturer's instruction. Then cDNA was synthesized using SUPERSCRIPT III® First-strand Synthesis System (catalog number: 18080-051, Invitrogen, USA) according to the manufacturer's instruction. Five μg of RNA was used for the synthesis per sample and a primer corresponding to a 3'-conserved site in each type subtype of the immunoglobulin gene was used instead of oligo-d(T). For example, For a heavy chain of IgM, MuIgMVH3'-1 was used and for a heavy chain of IgG, MuIgGVH3'-2 was used. Also, for kappa light chain MuIgkVL3'-1 was used and for lamda light chain MuIgλ VL3'-1 was used. These primers were from Ig-primer set (catalog number 69831-3, Novagen, USA) and the sequences are presented in Table 2 to 4.

TABLE 2

| Name | Base | Degeneracy | Position of the amino acid | Sequence (5'-3') | SEQ ID NO |
|---|---|---|---|---|---|
| MuIgV$_H$5'-A | 33 | 512 | -20 to -13 | GGGAATTC<u>ATG</u>GRASTTSKG GYTMARCTKGRTT | 15 |
| MuIgV$_H$5'-B | 34 | 64 | -20 to -13 | GGGAATTC<u>ATG</u>RAATGSASC TGGGTYWTYCTCTT | 16 |
| MuIgV$_H$5'-C | 39 | — | -20 to -11 | ACTAGTCGAC<u>ATG</u>GACTCCA GGCTCAATTTAGTTTTCCT | 17 |
| | 36 | 48 | -20 to -12 | ACTAGTCGAC<u>ATG</u>GCTGTCY TRGRGCTGYTCYTCTG | 18 |
| | 39 | 24 | -20 to -11 | ACTAGTCGAC<u>ATG</u>GVTTGGS TGGAMCTTGCYATTCCT | 19 |
| MuIgV$_H$5'-D | 36 | 8 | -20 to -12 | ACTAGTCGACATGAA<u>ATG</u>CA GCTGGRTYATSTTCTT | 20 |
| | 36 | 32 | -20 to -12 | ACTAGTCGAC<u>ATG</u>GRCARGC TTACYTYYTCATTCCT | 21 |
| | 36 | — | -20 to -12 | ACTAGTCGAC<u>ATG</u>ATGGTGT TAAGTCTTCTGTACCT | 22 |
| MuIgV$_H$5'-E | 36 | 8 | -20 to -12 | ACTAGTCGAC<u>ATG</u>GGATGGA GCTRTATCATSYTCTT | 23 |
| | 33 | 24 | -20 to -13 | ACTAGTCGAC<u>ATG</u>AAGWTGT GGBTRAACTGGRT | 24 |
| | 35 | 64 | -20 to -13 | ACTAGTCGAC<u>ATG</u>GRATGGA SCKKIRTCTTMTCT | 25 |
| MuIgV$_H$5'-F | 35 | 32 | -20 to -13 | ACTAGTCGAC<u>ATG</u>AACTTYG GGYTSAGMTTGRTTT | 26 |
| | 35 | — | -20 to -13 | ACTAGTCGAC<u>ATG</u>TACTTGG GACTGAGCTGTGTAT | 27 |
| | 33 | — | -20 to -13 | ACTAGTCGAC<u>ATG</u>AGAGTGC TGATTCTTTTGTG | 28 |
| | 38 | — | -20 to -12 | ACTAGTCGAC<u>ATG</u>GATTTTG GGCTGATTTTTTTATTG | 29 |
| MuIgMV$_H$3'-1 | 32 | — | 125 to 118 | CCCAAGCTTACGAGGGGGAA GACATTTGG<u>GAA</u> | 30 |

TABLE 3

| Name | Base | Degeneracy | Position of the amino acid | Sequence (5'-3') | SEQ ID NO |
|---|---|---|---|---|---|
| MuIgGV$_L$3'-2 | 35 | 32 | 126 to 119 | CCCAAGCTTCGAGGGRCCARR GGATARACIGRTGG | 31 |
| MuIgκV$_L$5'-A | 32 | 32 | -20 to -13 | GGGAATTC<u>ATG</u>RAGRCACARW CYCAGGTCTTT | 32 |
| MuIgκV$_L$5'-B | 33 | — | -20 to -13 | GGGAATTC<u>ATG</u>GAGACAGACA CACTCCTGCTAT | 33 |
| MuIgκV$_L$5'-C | 39 | 8 | -20 to -11 | ACTAGTCGAC<u>ATG</u>GAGWCAGA CACACTSCTGTYATGGGT | 34 |
| MuIgκV$_L$5'-D | 42 | 16 | -20 to -10 | ACTAGTCGAC<u>ATG</u>AGGRCCCC TGCTCAGWTTYTTGGIWTCTT | 35 |
| | 41 | 128 | -20 to -14 | ACTAGTCGAC<u>ATG</u>GGCWTCAA GATGRAGTCACAKWYYCWGG | 36 |
| MuIgκV$_L$5'-E | 39 | 4 | -20 to -11 | ACTAGTCGAC<u>ATG</u>AGTGTGCY CACTCAGGTCCTGGSGTT | 37 |
| | 41 | 32 | -15 to -5 | ACTAGTGGAC<u>ATG</u>TGGGGATC GKTTTYAMMCTTTTCAATTG | 38 |
| | 38 | — | -20 to -11 | ACTAGTCGAC<u>ATG</u>GAAGCCCC AGCTCAGCTTCTCTTCC | 39 |
| MuIgκV$_L$5'-F | 36 | 32 | -20 to -12 | ACTAGTCGAC<u>ATG</u>AGIMMKTC TMTTCATTTCYTGGG | 40 |
| | 36 | 96 | -20 to -12 | ACTAGTCGAC<u>ATG</u>AKGTMCYC TGCTCAGYTYCTIRG | 41 |

TABLE 3-continued

| Name | Base | Degeneracy | Position of the amino acid | Sequence (5'-3') | SEQ ID NO |
|---|---|---|---|---|---|
| | 35 | 8 | -20 to -12 | ACTAGTCGAC<u>ATG</u>GTRTCCWC ASCTCAGTTCCTTG | 42 |
| | 37 | — | -16 to -8 | ACTAGTCGAC<u>ATG</u>TATATATG TTTGTTGTCTATTTCT | 43 |
| MuIgκV<sub>L</sub>5'-G | 39 | — | -19 to -10 | ACTAGTCGAC<u>ATG</u>AAGTTGCC TGTTAGGCTGTTGGTGCT | 44 |
| | 39 | 8 | -22 to -13 | ACTAGTCGAC<u>ATG</u>GATTTWCA RGTGCAGATTWTCAGCTT | 45 |
| | 37 | 12 | -15 to -7 | ACTAGTCGAC<u>ATG</u>GTYCTYAT YTCCTTGCTGTTCTGG | 46 |
| | 37 | 24 | -15 to -7 | ACTCGTCGAC<u>ATG</u>GTYCTYAT YTTRCTGCTGCTATGG | 47 |

TABLE 4

| Name | Base | Degeneracy | Position of the amino acid | Sequence (5'-3') | SEQ ID NO |
|---|---|---|---|---|---|
| MuIgκV<sub>L</sub>3'-1 | 30 | — | 122 to 116 | CCCAAGCTTACTGGATG GTGGGAAGAT<u>GGA</u> | 48 |
| MuIgλV<sub>L</sub>5'-A | 33 | 128 | -20 to -13 | GGGAATTC<u>ATG</u>GCCTGG AYTYCWCTYQIMYTCT | 49 |
| MuIgλV<sub>L</sub>3'-1 | 32 | 32 | 125 to 118 | CCCAAGCTTAGCTCYTC WGWGGAIGGYGG<u>RAA</u> | 50 |

*Amino acid position of the primer relative to the start codon of the Ig variable region coding sequence Immunoglobulin-PCR The cDNA synthesized using the mouse Ig-primer set as described above and 2× PCR pre-mix (catalog number STD01-M50 h, SolGent, Korea) was used for Immunoglobulin-PCR. Different 5'-primers was used for PCR according to the subtype of immunoglobulin amplified. Specifically, for a heavy chain of IgG or IgM, MuIgV<sub>H</sub>5'-A, MuIgV<sub>H</sub>5'-B, MuIgV<sub>H</sub>5'-C, MuIgV<sub>H</sub>5'-D, MuIgV<sub>H</sub>5'-E and MuIgV<sub>H</sub>5'-F were used. For a kappa light chain, MuIgκV<sub>L</sub>5'-A, MuIgκV<sub>L</sub>5'-B, MuIgκV<sub>L</sub>5'-C, MuIgκV<sub>L</sub>5'-D, MuIgκV<sub>L</sub>5'-E, MuIgκV<sub>L</sub>5'-F and MuIgκV<sub>L</sub>5'-G were used as a 5'-primer. For a lamda light chain MuIgλV<sub>L</sub>5'-A was used (refer to Table 2).

The PCR conditions using 5'-primers of A and B was as follows: 94° C., 3 min→94° C., 1 min/50° C., 1 min/72° C., 2 min (35 cycles)→72° C., 6 min→4° C., termination.

The PCR conditions using 5'-primers of C-G was as follows: 94° C., 1 min/60° C., 1 min/72° C., 2 min (35 cycles)→72° C., 6 min→4° C., termination.

After the PCR reaction, the products were separated on a 2% DNA agarose gel. Then the amplified DNA was extracted from the gel using gel-elution method as described above.

Figure 2:
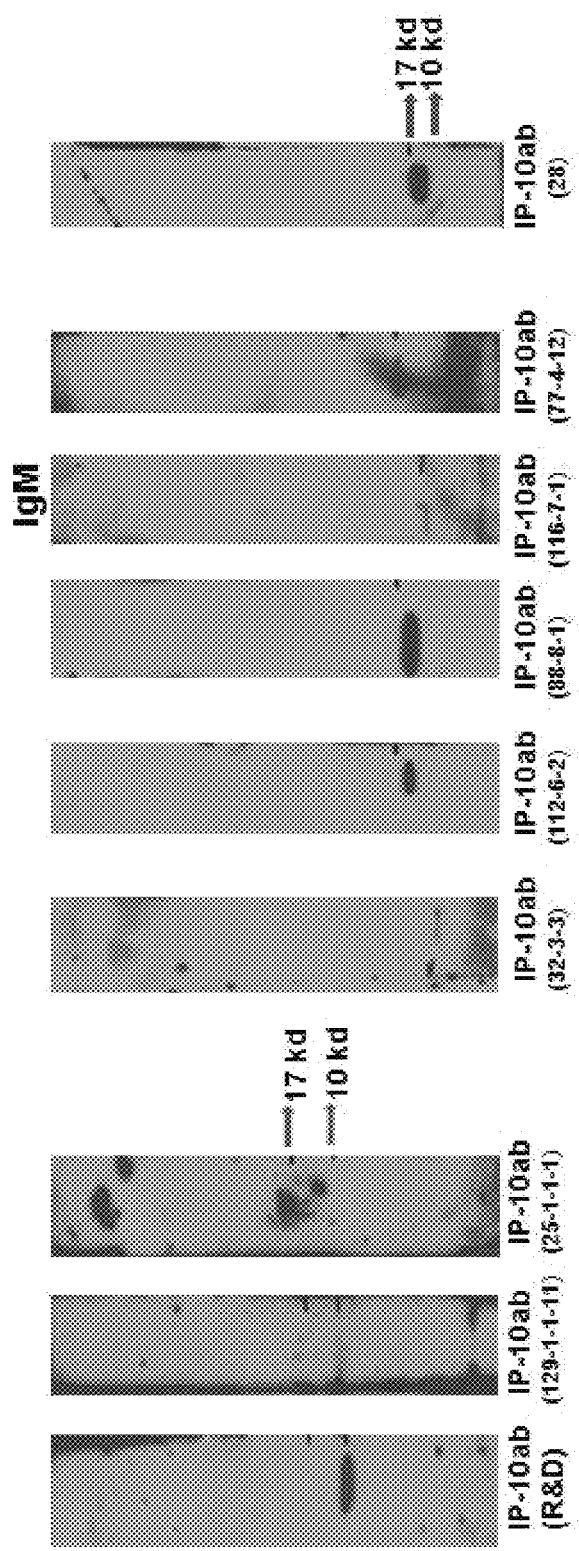
FIG. 2 is the result of a western blot analysis to assess the binding affinity of anti-IP-10 monoclonal antibody to IP-10 antigen, in which the antibody produced from the hybridoma according to one example of the present disclosure and recombinant human IP-10 (10 kb) was used and mouse IgG was used as a secondary antibody.

Results
Production of Anti-IP-10 Antibody from the Hybridoma Cell Line Established Anti-IP-10 monoclonal antibodies were prepared from the hybridoma cell line established as above. The antibodies produced were tested using a recombinant human IP-10 protein in a western blot and clones #25, #28, #77, #88, #112, #116 and #129 were confirmed to be positive for IP-10 antigen (FIG. 2).

Figure 12:
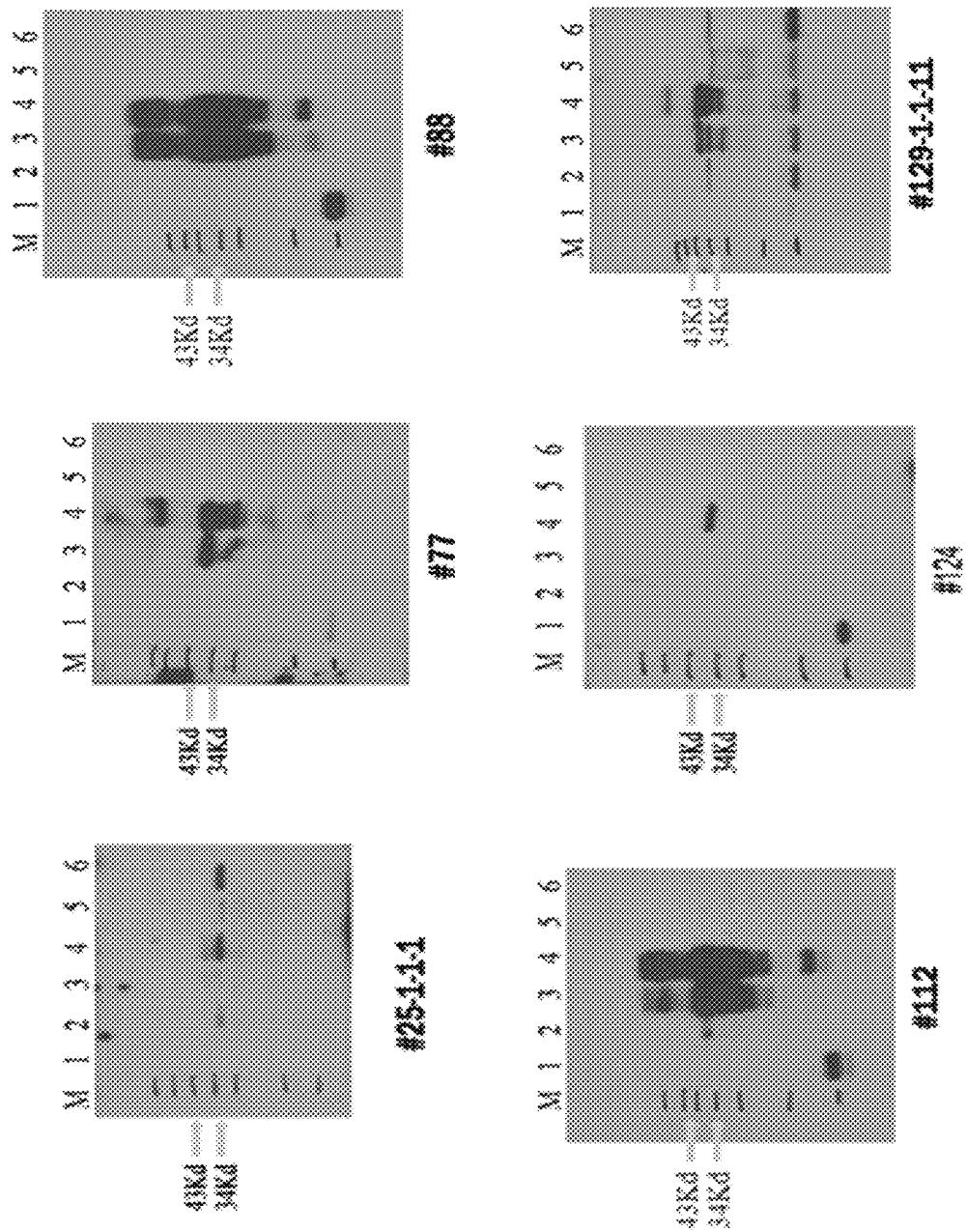
FIG. 12 shows the epitopes of IP-10 antigen to which anti-IP-10 monoclonal antibody binds, in which the lanes indicates: Lane: IP-10 recombinant protein; Lane 2: epitope 1 (amino acids 1-40), Lane 3: epitope 2 (amino acids 21-60), Lane 4: epitope 3 (amino acids 41-80), Lane 5: epitope 4 (amino acids 61-98), Lane 6: GST (negative control).

Then the sequence of the monoclonal antibodies #25, #28, #77, #88, #112, #116 and #129 were confirmed by PCR. The sequences are shown in Table 5. Also CDR 1-3 of heavy and light chain of the monoclonal antibodies are shown in FIGS. 12 and 13.

TABLE 5

| Monoclonal Ab | Heavy chain variable region | Light chain varaible region |
|---|---|---|
| #25 | 93 | 94 |
| #28 | 95 | 96 |
| #77 | 97 | 98 |
| #88 | 99 | 100 |
| #112 | 101 | 102 |
| #116 | 103 | 104 |
| #129 | 105 | 106 |

Cell Migration Assay

To test whether the anti-IP-10 antibody can inhibit the cell migration, cell migration assay was performed. Also, the epitope to which anti-IP-10 antibody recognized was also examined.

Figure 3:
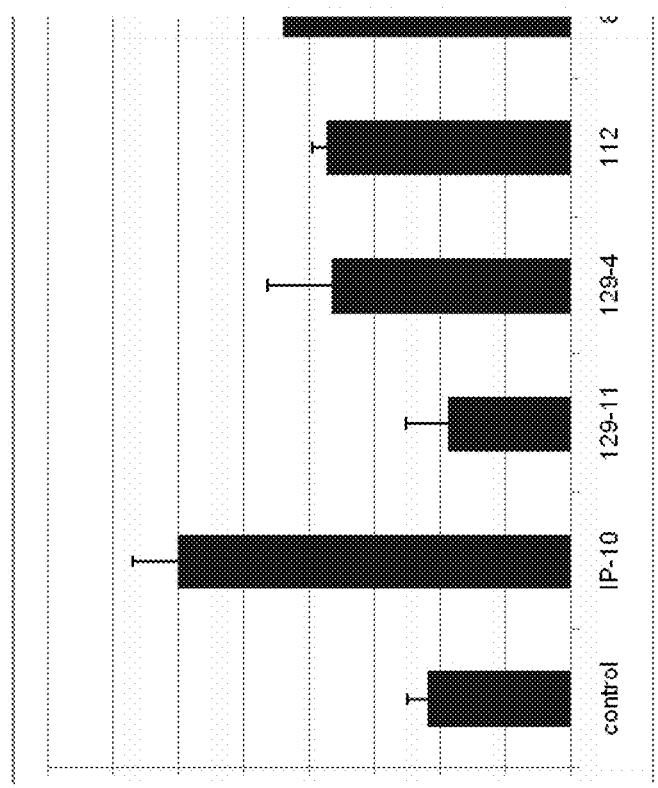
FIG. 3. is the result of cell migration assay of anti-IP-10 monoclonal antibody (200 ng/ml).
Figure 4:
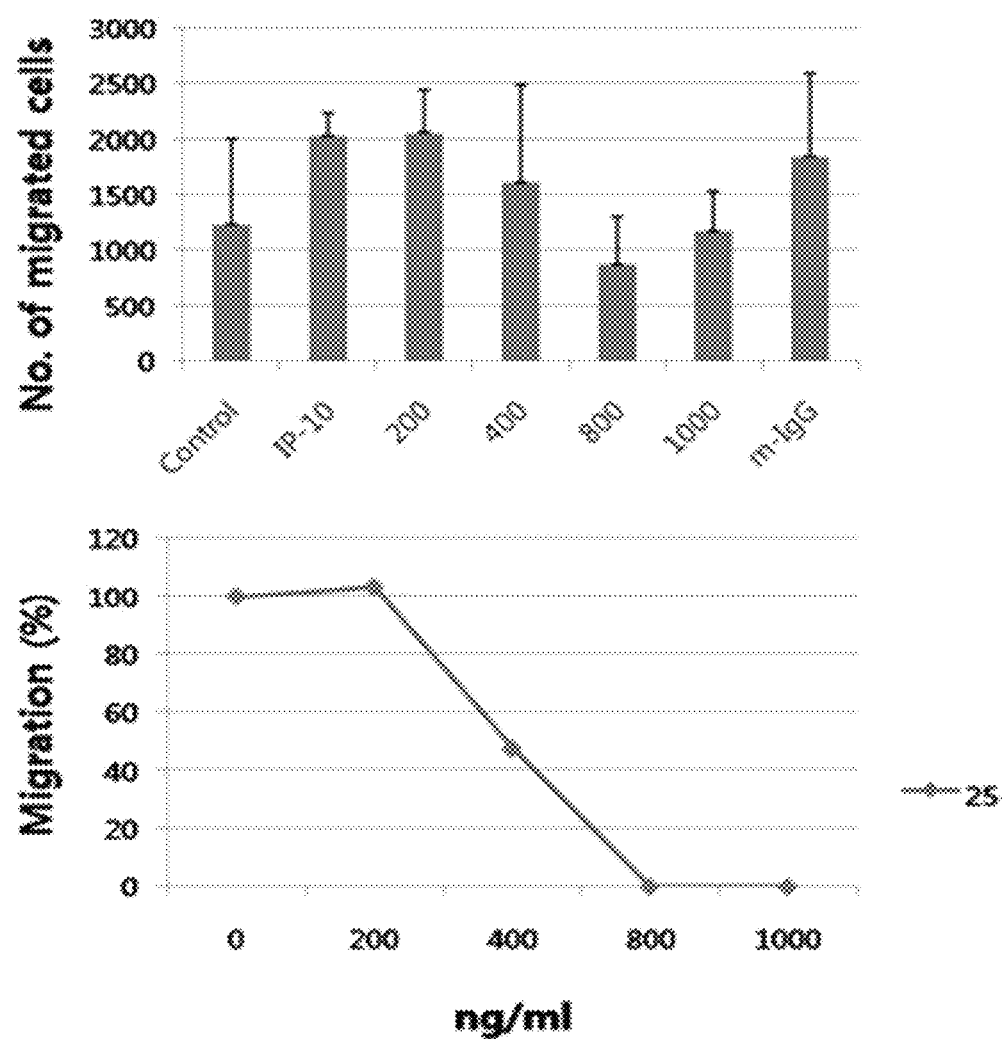
FIG. 4 is the result of a cell migration assay of anti-IP-10 monoclonal antibody #25.
Figure 6:
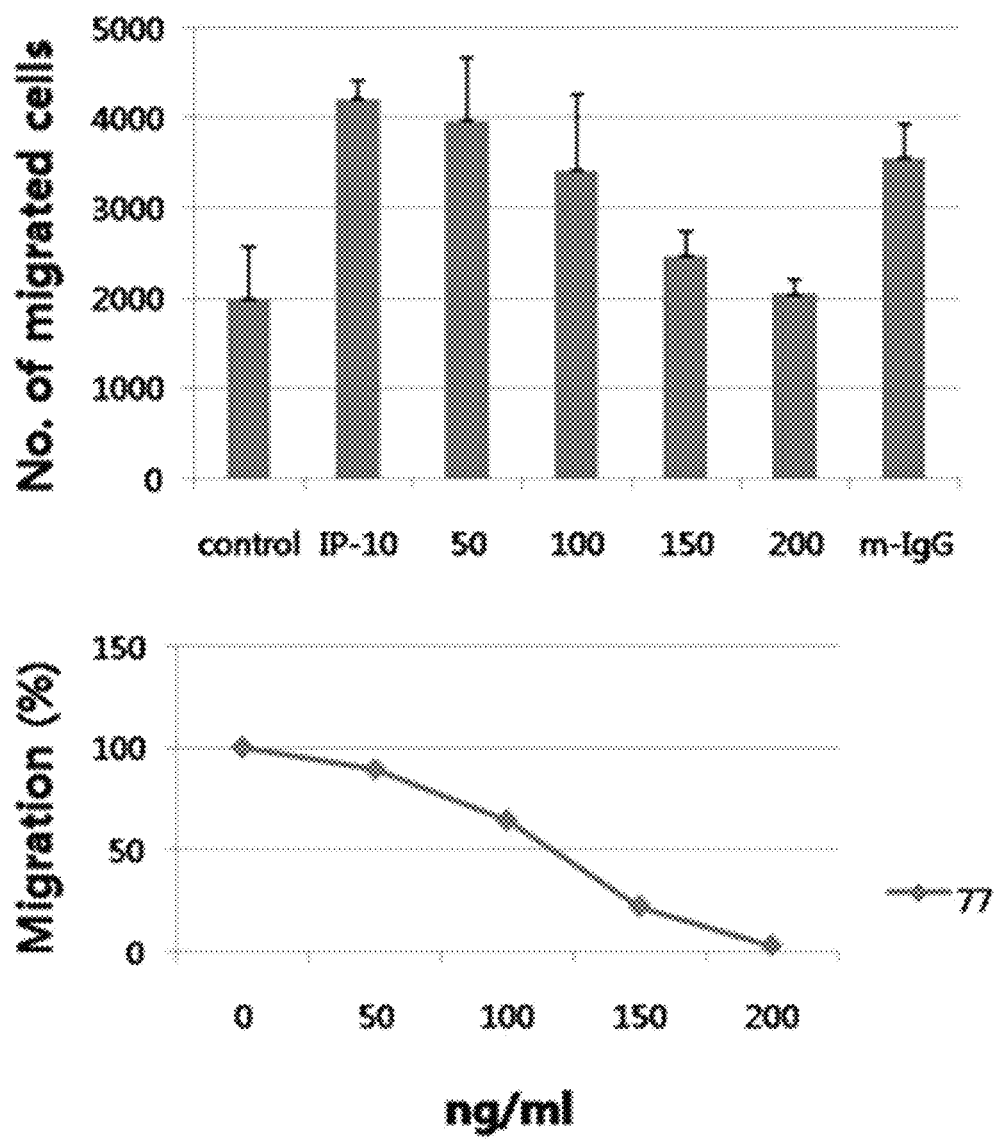
FIG. 6 is the result of a cell migration assay of anti-IP-10 monoclonal antibody #77.
Figure 7:
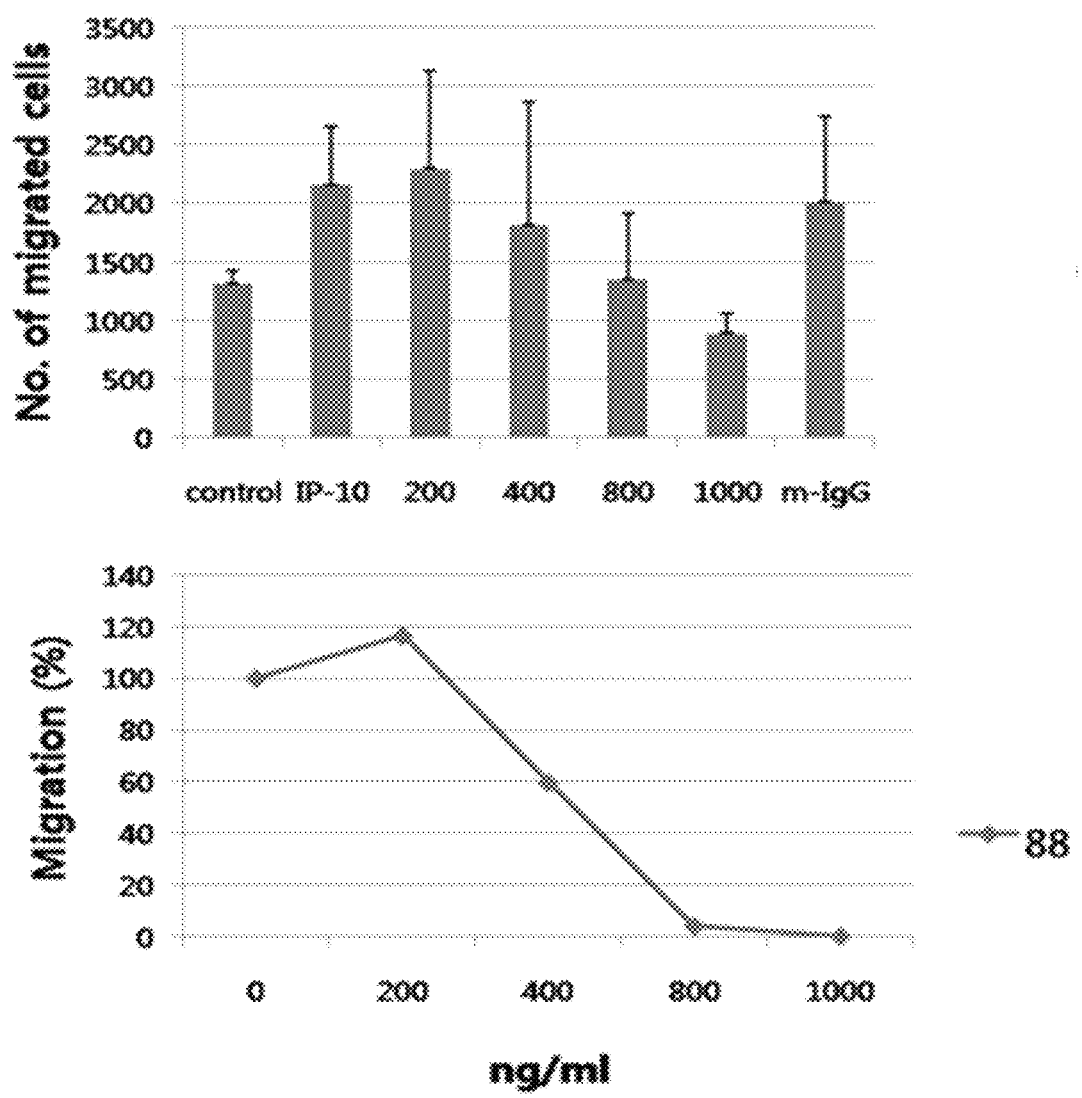
FIG. 7 is the result of a cell migration assay of anti-IP-10 monoclonal antibody #88.
Figure 8:
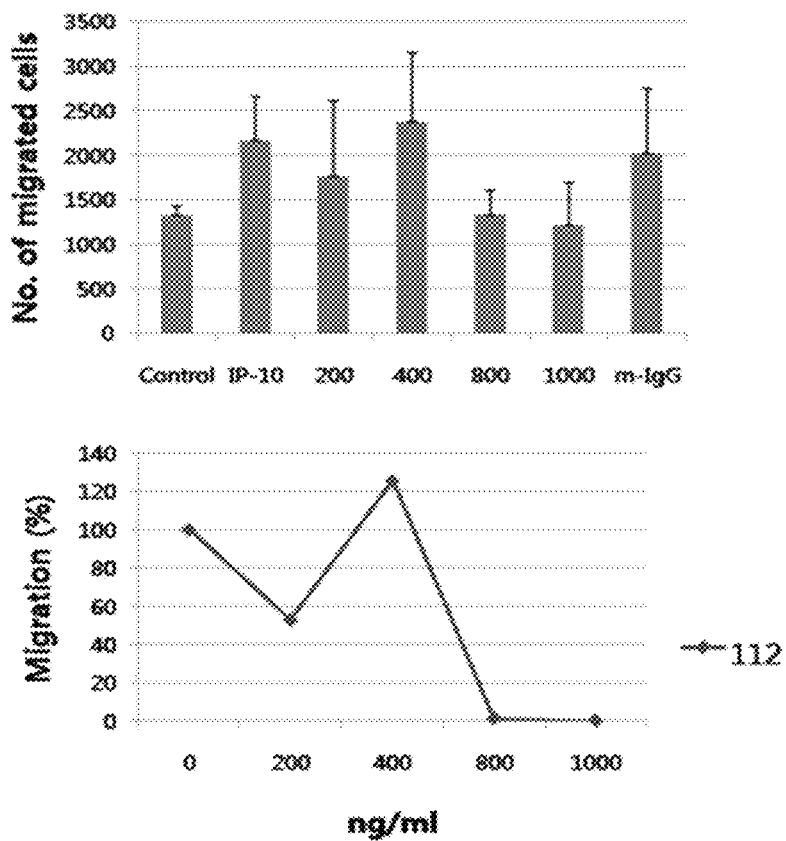
FIG. 8 is the result of a cell migration assay of anti-IP-10 monoclonal antibody #112.
Figure 9:
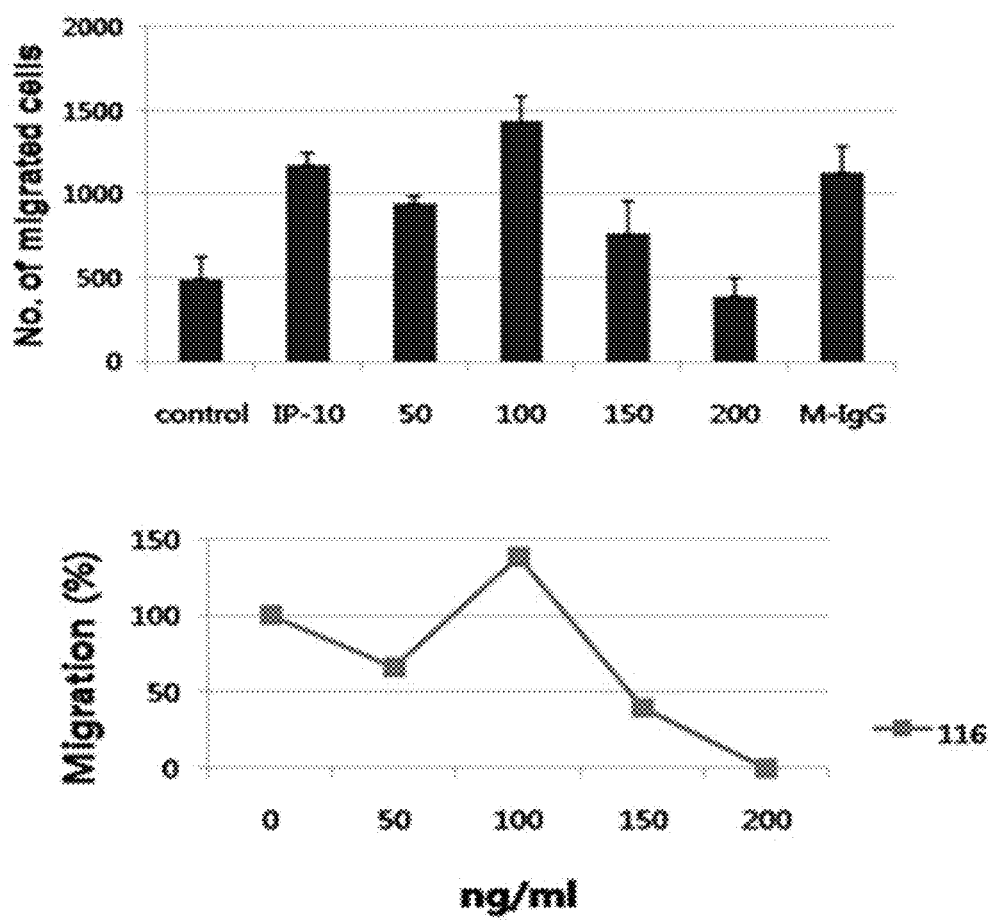
FIG. 9 is the result of a cell migration assay of anti-IP-10 monoclonal antibody #116

As shown in FIG. 3, anti-IP-10 monoclonal antibody can effectively inhibit the migration of the cells induced by IP-10. The inhibitory activity of each of the clone #25, #28, #77, #88, #112, #116 and #129 are shown in FIGS. 4 to 10. As shown in FIG. 5, the clone #28 completely inhibited the migration of the cells induced by IP-10 at the concentration above 150 ng/ml (FIG. 5). Also, the clone #28 was found to bind to epitope 4 (A61-A98) (FIG. 11).

Identification of Epitopes to which Anti-IP-10 Monoclonal Antibody Recognizes

Figure 11:
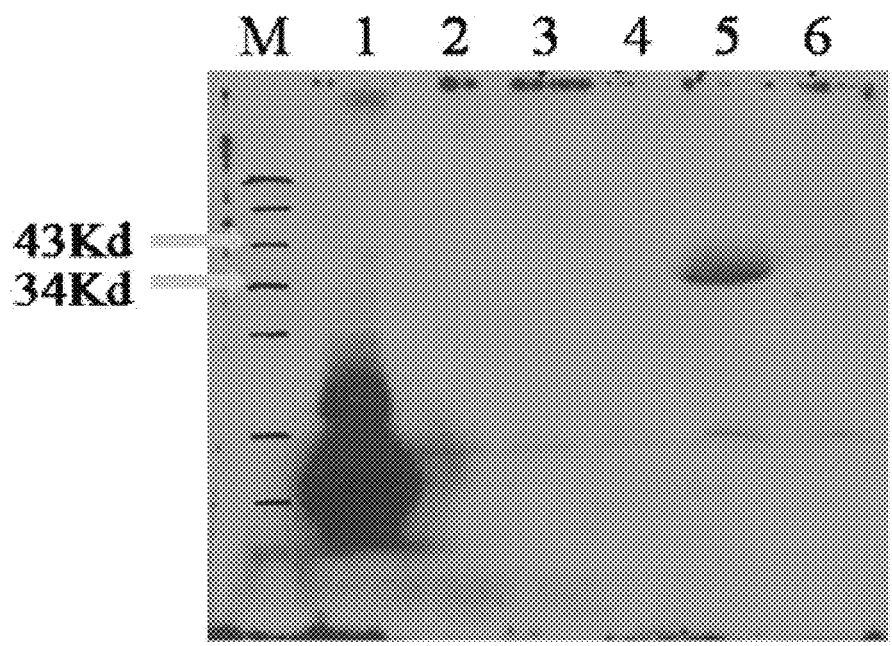
FIG. 11 is the result of a western blot analysis showing that anti-IP-10 monoclonal antibody #28 binds to epitope 4 (A61-98).

Epitopes to which anti-IP-10 monoclonal antibody binds are indicated in FIG. 11. As shown in FIG. 11, all anti-IP-10 monoclonal antibodies were found to recognize epitope 4, or both epitopes 3 and 4. In the present disclosure, since the four epitopes were designed to be partially overlapped as in FIG. 1, the results indicates that amino acids from 61 to 80 of IP-10 (SEQ ID NO: 6) are epitope for IP-10.

Although a few embodiments of the present disclosure have been shown and described, it would be appreciated by those skilled in the art that changes may be made in this embodiment without departing from the principles and sprit of the invention, the scope of which is defined in the claims and their equivalents.

What is claimed is:

1. An antibody or antigen-binding fragment thereof which specifically binds to an epitope of SEQ ID NO:5 wherein the antibody or the antigen-binding fragment comprises a heavy chain variable region and light chain variable region including the following CDR (Complementarity Determining Region) H1, H2 and H3 and CDR L1, L2 and L3:
   (i) CDR H1 of SEQ ID NO: 51, CDR H2 of SEQ ID NO: 52 and CDR H3 of SEQ ID NO: 53, and CDR L1 of SEQ ID NO: 72, CDR L2 of SEQ ID NO: 73 and CDR L3 of SEQ ID NO: 74;
   (ii) CDR H1 of SEQ ID NO: 54, CDR H2 of SEQ ID NO: 55 and CDR H3 of SEQ ID NO: 56, and CDR L1 of SEQ ID NO: 75, CDR L2 of SEQ ID NO: 76 and CDR L3 of SEQ ID NO: 77;
   (iii) CDR H1 of SEQ ID NO: 57, CDR H2 of SEQ ID NO: 58 and CDR H3 of SEQ ID NO: 59, and CDR L1 of SEQ ID NO: 78, CDR L2 of SEQ ID NO: 79 and CDR L3 of SEQ ID NO: 80;
   (iv) CDR H1 of SEQ ID NO: 60, CDR H2 of SEQ ID NO: 61 and CDR H3 of SEQ ID NO: 62, and CDR L1 of SEQ ID NO: 81, CDR L2 of SEQ ID NO: 82 and CDR L3 of SEQ ID NO: 83;
   (v) CDR H1 of SEQ ID NO: 63, CDR H2 of SEQ ID NO: 64 and CDR H3 of SEQ ID NO: 65, and CDR L1 of SEQ ID NO: 84, CDR L2 of SEQ ID NO: 85 and CDR L3 of SEQ ID NO: 86;
   (vi) CDR H1 of SEQ ID NO: 66, CDR H2 of SEQ ID NO: 67 and CDR H3 of SEQ ID NO: 68, and CDR L1 of SEQ ID NO: 87, CDR L2 of SEQ ID NO: 88 and CDR L3 of SEQ ID NO: 89; or
   (vii) CDR H1 of SEQ ID NO: 69, CDR H2 of SEQ ID NO: 70 and CDR H3 of SEQ ID NO: 71, and CDR L1 of SEQ ID NO: 90, CDR L2 of SEQ ID NO: 91 and CDR L3 of SEQ ID NO: 92.

2. The antibody or an antigen-binding fragment thereof of claim 1, wherein the antibody or the antigen-binding fragment comprises a heavy chain and a light chain, and the heavy chain and the light chain consist of the amino acid sequence set forth in SEQ ID NOs: (i) 93 and 94, (ii) 95 and 96, (iii) 97 and 98, (iv) 99 and 100, (v) 101 and 102, (vi) 103 and 104, or (vii) 105 and 106.

3. A nucleic acid molecule encoding the heavy chain variable and light chain variable region of the antibody or antigen-biding fragment thereof according to claim 1.

4. A nucleic acid molecule encoding the heavy chain and light chain of the antibody or antigen-biding fragment thereof according to claim 2.

5. A pharmaceutical composition comprising an antibody or antigen-binding fragment thereof according to claim 1 and a pharmaceutically acceptable carrier.

6. A pharmaceutical composition comprising an antibody or antigen-binding fragment thereof according to claim 2 and a pharmaceutically acceptable carrier.

* * * * *

```
                           SEQUENCE LISTING

<160> NUMBER OF SEQ ID NOS: 120

<210> SEQ ID NO 1
<211> LENGTH: 98
<212> TYPE: PRT
<213> ORGANISM: Homo sapiens

<400> SEQUENCE: 1

Met Asn Gln Thr Ala Ile Leu Ile Cys Cys Leu Ile Phe Leu Thr Leu
 1               5                  10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 2
<211> LENGTH: 40
<212> TYPE: PRT
<213> ORGANISM: Artificial Sequence
<220> FEATURE:
<223> OTHER INFORMATION: fragment 1 of IP-10

<400> SEQUENCE: 2

Met Asn Gln Thr Ala Ile Leu Ile Cys Cys Leu Ile Phe Leu Thr Leu
 1               5                  10                  15

Ser Gly Ile Gln Gly Val Pro Leu Ser Arg Thr Val Arg Cys Thr Cys
            20                  25                  30

Ile Ser Ile Ser Asn Gln Pro Val
        35                  40

<210> SEQ ID NO 3
<211> LENGTH: 40
<212> TYPE: PRT
<213> ORGANISM: Artificial Sequence
<220> FEATURE:
<223> OTHER INFORMATION: fragment 2 of IP-10

<400> SEQUENCE: 3

Gly Val Pro Leu Ser Arg Thr Val Arg Cys Thr Cys Ile Ser Ile Ser
 1               5                  10                  15

Asn Gln Pro Val Asn Pro Arg Ser Leu Glu Lys Leu Glu Ile Ile Pro
            20                  25                  30

Ala Ser Gln Phe Cys Pro Arg Val
        35                  40

<210> SEQ ID NO 4
<211> LENGTH: 40
<212> TYPE: PRT
<213> ORGANISM: Artificial Sequence
```

```
<220> FEATURE:
<223> OTHER INFORMATION: fragment 3 of IP-10

<400> SEQUENCE: 4

Asn Pro Arg Ser Leu Glu Lys Leu Glu Ile Ile Pro Ala Ser Gln Phe
 1               5                  10                  15

Cys Pro Arg Val Glu Ile Ile Ala Thr Met Lys Lys Lys Gly Glu Lys
             20                  25                  30

Arg Cys Leu Asn Pro Glu Ser Lys
         35                  40

<210> SEQ ID NO 5
<211> LENGTH: 38
<212> TYPE: PRT
<213> ORGANISM: Artificial Sequence
<220> FEATURE:
<223> OTHER INFORMATION: fragment 4 of IP-10

<400> SEQUENCE: 5

Glu Ile Ile Ala Thr Met Lys Lys Lys Gly Glu Lys Arg Cys Leu Asn
 1               5                  10                  15

Pro Glu Ser Lys Ala Ile Lys Asn Leu Leu Lys Ala Val Ser Lys Glu
             20                  25                  30

Arg Ser Lys Arg Ser Pro
         35

<210> SEQ ID NO 6
<211> LENGTH: 20
<212> TYPE: PRT
<213> ORGANISM: Artificial Sequence
<220> FEATURE:
<223> OTHER INFORMATION: epitope of IP-10

<400> SEQUENCE: 6

Glu Ile Ile Ala Thr Met Lys Lys Lys Gly Glu Lys Arg Cys Leu Asn
 1               5                  10                  15

Pro Glu Ser Lys
             20

<210> SEQ ID NO 7
<211> LENGTH: 26
<212> TYPE: DNA
<213> ORGANISM: Artificial Sequence
<220> FEATURE:
<223> OTHER INFORMATION: IP-10-segment 1 sense

<400> SEQUENCE: 7
gctagaattc atgaatcaaa ctgcca                                    26

<210> SEQ ID NO 8
<211> LENGTH: 24
<212> TYPE: DNA
<213> ORGANISM: Artificial Sequence
<220> FEATURE:
<223> OTHER INFORMATION: IP-10-segment 1 anti-sense

<400> SEQUENCE: 8
gatcctcgag aataggttga ttac                                      24

<210> SEQ ID NO 9
<211> LENGTH: 27
<212> TYPE: DNA
<213> ORGANISM: Artificial Sequence
<220> FEATURE:
```

```
<223> OTHER INFORMATION: IP-10-segment 2 sense

<400> SEQUENCE: 9
gctagaattc ggagtacctc tctctag                                          27

<210> SEQ ID NO 10
<211> LENGTH: 27
<212> TYPE: DNA
<213> ORGANISM: Artificial Sequence
<220> FEATURE:
<223> OTHER INFORMATION: IP-10-segment 2 anti-sense

<400> SEQUENCE: 10
atcctcgaga acacgtggac aaaattg                                          27

<210> SEQ ID NO 11
<211> LENGTH: 26
<212> TYPE: DNA
<213> ORGANISM: Artificial Sequence
<220> FEATURE:
<223> OTHER INFORMATION: IP-10-segment 3 sense

<400> SEQUENCE: 11
gctagaattc aatccaaggt ctttag                                           26

<210> SEQ ID NO 12
<211> LENGTH: 25
<212> TYPE: DNA
<213> ORGANISM: Artificial Sequence
<220> FEATURE:
<223> OTHER INFORMATION: IP-10-segment 3 anti-sense

<400> SEQUENCE: 12
atcctcgagc ttcgattctg gattc                                            25

<210> SEQ ID NO 13
<211> LENGTH: 28
<212> TYPE: DNA
<213> ORGANISM: Artificial Sequence
<220> FEATURE:
<223> OTHER INFORMATION: IP-10-segment 4 sense

<400> SEQUENCE: 13
gctagaattc gagatcattg ctacaatg                                         28

<210> SEQ ID NO 14
<211> LENGTH: 26
<212> TYPE: DNA
<213> ORGANISM: Artificial Sequence
<220> FEATURE:
<223> OTHER INFORMATION: IP-10-segment 4 anti-sense

<400> SEQUENCE: 14
gatcctcgag aggagatctt ttagag                                           26

<210> SEQ ID NO 15
<211> LENGTH: 33
<212> TYPE: DNA
<213> ORGANISM: Artificial Sequence
<220> FEATURE:
<223> OTHER INFORMATION: MuIgVH5'-A

<400> SEQUENCE: 15
gggaattcat grasttskgg ytmarctkgr ttt                                   33
```

<210> SEQ ID NO 16
<211> LENGTH: 34
<212> TYPE: DNA
<213> ORGANISM: Artificial Sequence
<220> FEATURE:
<223> OTHER INFORMATION: MuIgVH5'-B

<400> SEQUENCE: 16
gggaattcat graatgsasc tgggtywtyc tctt    34

<210> SEQ ID NO 17
<211> LENGTH: 39
<212> TYPE: DNA
<213> ORGANISM: Artificial Sequence
<220> FEATURE:
<223> OTHER INFORMATION: MuIgVH5'-C

<400> SEQUENCE: 17
actagtcgac atggactcca ggctcaattt agttttcct    39

<210> SEQ ID NO 18
<211> LENGTH: 36
<212> TYPE: DNA
<213> ORGANISM: Artificial Sequence
<220> FEATURE:
<223> OTHER INFORMATION: MuIgVH5'-C

<400> SEQUENCE: 18
actagtcgac atggctgtcy trgbgctgyt cytctg    36

<210> SEQ ID NO 19
<211> LENGTH: 37
<212> TYPE: DNA
<213> ORGANISM: Artificial Sequence
<220> FEATURE:
<223> OTHER INFORMATION: MuIgVH5'-C

<400> SEQUENCE: 19
actagtcgac atggvttggs tggamcttgc yattcct    37

<210> SEQ ID NO 20
<211> LENGTH: 36
<212> TYPE: DNA
<213> ORGANISM: Artificial Sequence
<220> FEATURE:
<223> OTHER INFORMATION: MuIgVH5'-D

<400> SEQUENCE: 20
actagtcgac atgaaatgca gctggrtyat sttctt    36

<210> SEQ ID NO 21
<211> LENGTH: 36
<212> TYPE: DNA
<213> ORGANISM: Artificial Sequence
<220> FEATURE:
<223> OTHER INFORMATION: MuIgVH5'-D

<400> SEQUENCE: 21
actagtcgac atggrcargc ttacwtyytc attcct    36

<210> SEQ ID NO 22
<211> LENGTH: 36
<212> TYPE: DNA
<213> ORGANISM: Artificial Sequence
<220> FEATURE:
<223> OTHER INFORMATION: MuIgVH5'-D

```
<400> SEQUENCE: 22
actagtcgac atgatggtgt taagtcttct gtacct                                 36

<210> SEQ ID NO 23
<211> LENGTH: 36
<212> TYPE: DNA
<213> ORGANISM: Artificial Sequence
<220> FEATURE:
<223> OTHER INFORMATION: MuIgVH5'-E

<400> SEQUENCE: 23
actagtcgac atgggatgga gctrtatcat sytctt                                 36

<210> SEQ ID NO 24
<211> LENGTH: 33
<212> TYPE: DNA
<213> ORGANISM: Artificial Sequence
<220> FEATURE:
<223> OTHER INFORMATION: MuIgVH5'-E

<400> SEQUENCE: 24
actagtcgac atgaagwtgt ggbtraactg grt                                    33

<210> SEQ ID NO 25
<211> LENGTH: 33
<212> TYPE: DNA
<213> ORGANISM: Artificial Sequence
<220> FEATURE:
<223> OTHER INFORMATION: MuIgVH5'-E

<400> SEQUENCE: 25
actagtcgac atggratgga sckkrtcttm tct                                    33

<210> SEQ ID NO 26
<211> LENGTH: 35
<212> TYPE: DNA
<213> ORGANISM: Artificial Sequence
<220> FEATURE:
<223> OTHER INFORMATION: MuIgVH5'-F

<400> SEQUENCE: 26
actagtcgac atgaacttyg ggytsagmtt grttt                                  35

<210> SEQ ID NO 27
<211> LENGTH: 35
<212> TYPE: DNA
<213> ORGANISM: Artificial Sequence
<220> FEATURE:
<223> OTHER INFORMATION: MuIgVH5'-F

<400> SEQUENCE: 27
actagtcgac atgtacttgg gactgagctg tgtat                                  35

<210> SEQ ID NO 28
<211> LENGTH: 33
<212> TYPE: DNA
<213> ORGANISM: Artificial Sequence
<220> FEATURE:
<223> OTHER INFORMATION: MuIgVH5'-F

<400> SEQUENCE: 28
actagtcgac atgagagtgc tgattctttt gtg                                    33

<210> SEQ ID NO 29
<211> LENGTH: 38
```

```
<212> TYPE: DNA
<213> ORGANISM: Artificial Sequence
<220> FEATURE:
<223> OTHER INFORMATION: MuIgVH5'-F

<400> SEQUENCE: 29
actagtcgac atggattttg ggctgattt ttttattg                              38

<210> SEQ ID NO 30
<211> LENGTH: 32
<212> TYPE: DNA
<213> ORGANISM: Artificial Sequence
<220> FEATURE:
<223> OTHER INFORMATION: MuIgMVH3'-1

<400> SEQUENCE: 30
cccaagctta cgagggggaa gacatttggg aa                                   32

<210> SEQ ID NO 31
<211> LENGTH: 35
<212> TYPE: DNA
<213> ORGANISM: Artificial Sequence
<220> FEATURE:
<223> OTHER INFORMATION: MuIgGVH3'-2
<220> FEATURE:
<221> NAME/KEY: variation
<222> LOCATION: (30)
<223> OTHER INFORMATION: a,t,c or g

<400> SEQUENCE: 31
cccaagcttc cagggrccar kggataracn grtgg                                35

<210> SEQ ID NO 32
<211> LENGTH: 32
<212> TYPE: DNA
<213> ORGANISM: Artificial Sequence
<220> FEATURE:
<223> OTHER INFORMATION: MuIgkVL5'-A

<400> SEQUENCE: 32
gggaattcat gragwcacak wcycaggtct tt                                   32

<210> SEQ ID NO 33
<211> LENGTH: 33
<212> TYPE: DNA
<213> ORGANISM: Artificial Sequence
<220> FEATURE:
<223> OTHER INFORMATION: MuIgkVL5'-B

<400> SEQUENCE: 33
gggaattcat ggagacagac acactcctgc tat                                  33

<210> SEQ ID NO 34
<211> LENGTH: 39
<212> TYPE: DNA
<213> ORGANISM: Artificial Sequence
<220> FEATURE:
<223> OTHER INFORMATION: MuIgkVL5'-C

<400> SEQUENCE: 34
actagtcgac atggagwcag acacactsct gtyatgggt                            39

<210> SEQ ID NO 35
<211> LENGTH: 42
<212> TYPE: DNA
<213> ORGANISM: Artificial Sequence
<220> FEATURE:
```

<223> OTHER INFORMATION: MuIgkVL5'-D
<220> FEATURE:
<221> NAME/KEY: variation
<222> LOCATION: (37)
<223> OTHER INFORMATION: a,t,c or g

<400> SEQUENCE: 35
actagtcgac atgaggrccc ctgctcagwt tyttggnwtc tt                42

<210> SEQ ID NO 36
<211> LENGTH: 41
<212> TYPE: DNA
<213> ORGANISM: Artificial Sequence
<220> FEATURE:
<223> OTHER INFORMATION: MuIgkVL5'-D

<400> SEQUENCE: 36
actagtcgac atgggcwtca agatgragtc acakwyycwg g                 41

<210> SEQ ID NO 37
<211> LENGTH: 39
<212> TYPE: DNA
<213> ORGANISM: Artificial Sequence
<220> FEATURE:
<223> OTHER INFORMATION: MuIgkVL5'-E

<400> SEQUENCE: 37
actagtcgac atgagtgtgc ycactcaggt cctggsgtt                    39

<210> SEQ ID NO 38
<211> LENGTH: 41
<212> TYPE: DNA
<213> ORGANISM: Artificial Sequence
<220> FEATURE:
<223> OTHER INFORMATION: MuIgkVL5'-E

<400> SEQUENCE: 38
actagtcgac atgtggggat cgktttyamm cttttcaatt g                 41

<210> SEQ ID NO 39
<211> LENGTH: 38
<212> TYPE: DNA
<213> ORGANISM: Artificial Sequence
<220> FEATURE:
<223> OTHER INFORMATION: MuIgkVL5'-E

<400> SEQUENCE: 39
actagtcgac atggaagccc cagctcagct tctcttcc                     38

<210> SEQ ID NO 40
<211> LENGTH: 36
<212> TYPE: DNA
<213> ORGANISM: Artificial Sequence
<220> FEATURE:
<223> OTHER INFORMATION: MuIgkVL5'-F
<220> FEATURE:
<221> NAME/KEY: variation
<222> LOCATION: (16)
<223> OTHER INFORMATION: a,t,c or g
<220> FEATURE:
<221> NAME/KEY: variation
<222> LOCATION: (22)
<223> OTHER INFORMATION: a,t,c or g
<220> FEATURE:
<221> NAME/KEY: variation
<222> LOCATION: (28)
<223> OTHER INFORMATION: a,t,c or g

<400> SEQUENCE: 40
actagtcgac atgagnmmkt cnmttcantt cytggg                36

<210> SEQ ID NO 41
<211> LENGTH: 36
<212> TYPE: DNA
<213> ORGANISM: Artificial Sequence
<220> FEATURE:
<223> OTHER INFORMATION: MuIgkVL5'-F
<220> FEATURE:
<221> NAME/KEY: variation
<222> LOCATION: (22)
<223> OTHER INFORMATION: a,t,c or g
<220> FEATURE:
<221> NAME/KEY: variation
<222> LOCATION: (34)
<223> OTHER INFORMATION: a,t,c or g

<400> SEQUENCE: 41
actagtcgac atgakgthcy cngctcagyt yctnrg                36

<210> SEQ ID NO 42
<211> LENGTH: 35
<212> TYPE: DNA
<213> ORGANISM: Artificial Sequence
<220> FEATURE:
<223> OTHER INFORMATION: MuIgkVL5'-F

<400> SEQUENCE: 42
actagtcgac atggtrtccw casctcagtt ccttg                 35

<210> SEQ ID NO 43
<211> LENGTH: 37
<212> TYPE: DNA
<213> ORGANISM: Artificial Sequence
<220> FEATURE:
<223> OTHER INFORMATION: MuIgkVL5'-F

<400> SEQUENCE: 43
actagtcgac atgtatatat gtttgttgtc tatttct               37

<210> SEQ ID NO 44
<211> LENGTH: 39
<212> TYPE: DNA
<213> ORGANISM: Artificial Sequence
<220> FEATURE:
<223> OTHER INFORMATION: MuIgkVL5'-G

<400> SEQUENCE: 44
actagtcgac atgaagttgc ctgttaggct gttggtgct             39

<210> SEQ ID NO 45
<211> LENGTH: 39
<212> TYPE: DNA
<213> ORGANISM: Artificial Sequence
<220> FEATURE:
<223> OTHER INFORMATION: MuIgkVL5'-G
<220> FEATURE:
<221> NAME/KEY: variation
<222> LOCATION: (18)
<223> OTHER INFORMATION: a,t,c or g

<400> SEQUENCE: 45
actagtcgac atggattnwc argtgcagat twtcagctt             39

<210> SEQ ID NO 46
<211> LENGTH: 37
<212> TYPE: DNA

```
<213> ORGANISM: Artificial Sequence
<220> FEATURE:
<223> OTHER INFORMATION: MuIgkVL5'-G

<400> SEQUENCE: 46
actagtcgac atggtyctya tvtccttgct gttctgg                           37

<210> SEQ ID NO 47
<211> LENGTH: 37
<212> TYPE: DNA
<213> ORGANISM: Artificial Sequence
<220> FEATURE:
<223> OTHER INFORMATION: MuIgkVL5'-G

<400> SEQUENCE: 47
actcgtcgac atggtyctya tvttrctgct gctatgg                           37

<210> SEQ ID NO 48
<211> LENGTH: 30
<212> TYPE: DNA
<213> ORGANISM: Artificial Sequence
<220> FEATURE:
<223> OTHER INFORMATION: MuIglVL3'-1

<400> SEQUENCE: 48
cccaagctta ctggatggtg ggaagatgga                                   30

<210> SEQ ID NO 49
<211> LENGTH: 33
<212> TYPE: DNA
<213> ORGANISM: Artificial Sequence
<220> FEATURE:
<223> OTHER INFORMATION: MuIgVL5'-A
<220> FEATURE:
<221> NAME/KEY: variation
<222> LOCATION: (28)
<223> OTHER INFORMATION: a,t,c or g

<400> SEQUENCE: 49
gggaattcat ggcctggayt ycwctywnmy tct                               33

<210> SEQ ID NO 50
<211> LENGTH: 32
<212> TYPE: DNA
<213> ORGANISM: Artificial Sequence
<220> FEATURE:
<223> OTHER INFORMATION: MuIgVL3'-1
<220> FEATURE:
<221> NAME/KEY: variation
<222> LOCATION: (24)
<223> OTHER INFORMATION: a,t,c or g

<400> SEQUENCE: 50
cccaagctta gctcytcwgw gganggyggr aa                                32

<210> SEQ ID NO 51
<211> LENGTH: 5
<212> TYPE: PRT
<213> ORGANISM: Artificial Sequence
<220> FEATURE:
<223> OTHER INFORMATION: CDRH1 of H25G

<400> SEQUENCE: 51

Gly Tyr Asn Met Asn
 1               5

<210> SEQ ID NO 52
```

-continued

```
<211> LENGTH: 17
<212> TYPE: PRT
<213> ORGANISM: Artificial Sequence
<220> FEATURE:
<223> OTHER INFORMATION: CDRH2 of H25G

<400> SEQUENCE: 52

Asn Ile Asp Pro Tyr Tyr Gly Gly Thr Ser Tyr Asn Gln Lys Phe Lys
1               5                   10                  15
Gly

<210> SEQ ID NO 53
<211> LENGTH: 9
<212> TYPE: PRT
<213> ORGANISM: Artificial Sequence
<220> FEATURE:
<223> OTHER INFORMATION: CDRH3 of H25G

<400> SEQUENCE: 53

Ser Gly Thr Ala Trp Phe Ala Tyr Trp
1               5

<210> SEQ ID NO 54
<211> LENGTH: 5
<212> TYPE: PRT
<213> ORGANISM: Artificial Sequence
<220> FEATURE:
<223> OTHER INFORMATION: CDRH1 of H28G

<400> SEQUENCE: 54

Asp Tyr Tyr Met Ser
1               5

<210> SEQ ID NO 55
<211> LENGTH: 19
<212> TYPE: PRT
<213> ORGANISM: Artificial Sequence
<220> FEATURE:
<223> OTHER INFORMATION: CDRH2 of H28G

<400> SEQUENCE: 55

Phe Ile Arg Asn Lys Ala Asn Gly Tyr Thr Thr Glu Tyr Ser Ala Ser
1               5                   10                  15
Val Lys Gly

<210> SEQ ID NO 56
<211> LENGTH: 13
<212> TYPE: PRT
<213> ORGANISM: Artificial Sequence
<220> FEATURE:
<223> OTHER INFORMATION: CDRH3 of H28G

<400> SEQUENCE: 56

Asp Pro Thr Ile Gly Thr Val Leu Cys Tyr Gly Leu Leu
1               5                   10

<210> SEQ ID NO 57
<211> LENGTH: 5
<212> TYPE: PRT
<213> ORGANISM: Artificial Sequence
<220> FEATURE:
<223> OTHER INFORMATION: CDRH1 of H77G

<400> SEQUENCE: 57

Asp Tyr Ser Met His
1               5
```

```
<210> SEQ ID NO 58
<211> LENGTH: 17
<212> TYPE: PRT
<213> ORGANISM: Artificial Sequence
<220> FEATURE:
<223> OTHER INFORMATION: CDRH2 of H77G

<400> SEQUENCE: 58

Trp Ile Asn Thr Glu Thr Gly Glu Pro Thr Tyr Ala Asp Asp Phe Lys
 1               5                  10                  15
Gly

<210> SEQ ID NO 59
<211> LENGTH: 11
<212> TYPE: PRT
<213> ORGANISM: Artificial Sequence
<220> FEATURE:
<223> OTHER INFORMATION: CDRH3 of H77G

<400> SEQUENCE: 59

Met Tyr Asp Tyr Ser Tyr Tyr Phe Asp Tyr Trp
 1               5                  10

<210> SEQ ID NO 60
<211> LENGTH: 5
<212> TYPE: PRT
<213> ORGANISM: Artificial Sequence
<220> FEATURE:
<223> OTHER INFORMATION: CDRH1 of H88G

<400> SEQUENCE: 60

Gly Tyr Ala Met Ser
 1               5

<210> SEQ ID NO 61
<211> LENGTH: 17
<212> TYPE: PRT
<213> ORGANISM: Artificial Sequence
<220> FEATURE:
<223> OTHER INFORMATION: CDRH2 of H88G

<400> SEQUENCE: 61

Ser Ile Thr Ser Gly Gly Ser Tyr Thr Ser Tyr Pro Asp Asn Met Lys
 1               5                  10                  15
Gly

<210> SEQ ID NO 62
<211> LENGTH: 12
<212> TYPE: PRT
<213> ORGANISM: Artificial Sequence
<220> FEATURE:
<223> OTHER INFORMATION: CDRH3 of H88G

<400> SEQUENCE: 62

His Ser Pro Val Ile Ala Ser Trp Phe Ala Tyr Trp
 1               5                  10

<210> SEQ ID NO 63
<211> LENGTH: 7
<212> TYPE: PRT
<213> ORGANISM: Artificial Sequence
<220> FEATURE:
<223> OTHER INFORMATION: CDRH1 of H112G

<400> SEQUENCE: 63
```

Thr Ser Gly Met Gly Val Gly
1               5

<210> SEQ ID NO 64
<211> LENGTH: 16
<212> TYPE: PRT
<213> ORGANISM: Artificial Sequence
<220> FEATURE:
<223> OTHER INFORMATION: CDRH2 of H112G

<400> SEQUENCE: 64

His Ile Trp Trp Asp Asp Asp Lys Phe Tyr Asn Pro Ser Leu Lys Ser
1               5                   10                  15

<210> SEQ ID NO 65
<211> LENGTH: 12
<212> TYPE: PRT
<213> ORGANISM: Artificial Sequence
<220> FEATURE:
<223> OTHER INFORMATION: CDRH3 of H112G

<400> SEQUENCE: 65

Arg Ala Phe Ser Ser Ser Ala Trp Phe Ala Tyr Trp
1               5                   10

<210> SEQ ID NO 66
<211> LENGTH: 5
<212> TYPE: PRT
<213> ORGANISM: Artificial Sequence
<220> FEATURE:
<223> OTHER INFORMATION: CDRH1 of H116M

<400> SEQUENCE: 66

Ser Ser Trp Met Asn
1               5

<210> SEQ ID NO 67
<211> LENGTH: 17
<212> TYPE: PRT
<213> ORGANISM: Artificial Sequence
<220> FEATURE:
<223> OTHER INFORMATION: CDRH2 of H116M

<400> SEQUENCE: 67

Arg Ile Tyr Pro Gly Asp Gly Asp Thr Asn Tyr Asn Gly Lys Phe Lys
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: CDRH3 of H116M

<400> SEQUENCE: 68

Ile Gly Asn Tyr Tyr Gly Ser Ser Tyr Leu Tyr Trp Tyr Phe Asp Val
1               5                   10                  15

Trp

<210> SEQ ID NO 69
<211> LENGTH: 5
<212> TYPE: PRT
<213> ORGANISM: Artificial Sequence
<220> FEATURE:

<223> OTHER INFORMATION: CDRH1 of H129G

<400> SEQUENCE: 69

Ser Tyr Gly Val His
1               5

<210> SEQ ID NO 70
<211> LENGTH: 16
<212> TYPE: PRT
<213> ORGANISM: Artificial Sequence
<220> FEATURE:
<223> OTHER INFORMATION: CDRH2 of H129G

<400> SEQUENCE: 70

Val Ile Trp Ser Gly Gly Ser Thr Asp Tyr Asn Ala Ala Phe Ile Ser
1               5                   10                  15

<210> SEQ ID NO 71
<211> LENGTH: 8
<212> TYPE: PRT
<213> ORGANISM: Artificial Sequence
<220> FEATURE:
<223> OTHER INFORMATION: CDRH3 of H129G

<400> SEQUENCE: 71

Asn Trp Gly Ala Met Asp Tyr Trp
1               5

<210> SEQ ID NO 72
<211> LENGTH: 13
<212> TYPE: PRT
<213> ORGANISM: Artificial Sequence
<220> FEATURE:
<223> OTHER INFORMATION: CDRL1 of L25k

<400> SEQUENCE: 72

Ala Thr Ser Gly Phe Thr Phe Thr Asp Tyr Tyr Met Ser
1               5                   10

<210> SEQ ID NO 73
<211> LENGTH: 14
<212> TYPE: PRT
<213> ORGANISM: Artificial Sequence
<220> FEATURE:
<223> OTHER INFORMATION: CDRL2 of L25k

<400> SEQUENCE: 73

Ile Arg Asn Lys Ala Asn Gly Tyr Thr Thr Glu Tyr Ser Ala
1               5                   10

<210> SEQ ID NO 74
<211> LENGTH: 9
<212> TYPE: PRT
<213> ORGANISM: Artificial Sequence
<220> FEATURE:
<223> OTHER INFORMATION: CDRL3 of L25k

<400> SEQUENCE: 74

Ala Arg Asp Pro Thr Ile Gly Thr Val
1               5

<210> SEQ ID NO 75
<211> LENGTH: 9
<212> TYPE: PRT
<213> ORGANISM: Artificial Sequence
<220> FEATURE:
<223> OTHER INFORMATION: CDRL1 of L28k

<400> SEQUENCE: 75

Ala Ser Ser Ser Val Ser Tyr Met Tyr
1               5

<210> SEQ ID NO 76
<211> LENGTH: 7
<212> TYPE: PRT
<213> ORGANISM: Artificial Sequence
<220> FEATURE:
<223> OTHER INFORMATION: CDRL2 of L28k

<400> SEQUENCE: 76

Arg Thr Ser Asn Leu Ala Ser
1               5

<210> SEQ ID NO 77
<211> LENGTH: 9
<212> TYPE: PRT
<213> ORGANISM: Artificial Sequence
<220> FEATURE:
<223> OTHER INFORMATION: CDRL3 of L28k

<400> SEQUENCE: 77

Gln Gln Tyr His Ser Tyr Pro Phe Thr
1               5

<210> SEQ ID NO 78
<211> LENGTH: 11
<212> TYPE: PRT
<213> ORGANISM: Artificial Sequence
<220> FEATURE:
<223> OTHER INFORMATION: CDRL1 of L77k

<400> SEQUENCE: 78

Arg Ala Ser Glu Asn Ile Tyr Ser Asn Leu Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: CDRL2 of L77k

<400> SEQUENCE: 79

Ala Ala Thr Asn Leu Ala Asp
1               5

<210> SEQ ID NO 80
<211> LENGTH: 9
<212> TYPE: PRT
<213> ORGANISM: Artificial Sequence
<220> FEATURE:
<223> OTHER INFORMATION: CDRL3 of L77k

<400> SEQUENCE: 80

Gln His Phe Trp Gly Thr Pro Tyr Thr
1               5

<210> SEQ ID NO 81
<211> LENGTH: 16
<212> TYPE: PRT
<213> ORGANISM: Artificial Sequence
<220> FEATURE:
<223> OTHER INFORMATION: CDRL1 of L88k

```
<400> SEQUENCE: 81

Arg Ser Ser Gln Ser Ile Val His Ser Asn Gly Asn Thr Tyr Leu Glu
1               5                   10                  15

<210> SEQ ID NO 82
<211> LENGTH: 7
<212> TYPE: PRT
<213> ORGANISM: Artificial Sequence
<220> FEATURE:
<223> OTHER INFORMATION: CDRL2 of L88k

<400> SEQUENCE: 82

Lys Val Ser Asn Arg Phe Ser
1               5

<210> SEQ ID NO 83
<211> LENGTH: 9
<212> TYPE: PRT
<213> ORGANISM: Artificial Sequence
<220> FEATURE:
<223> OTHER INFORMATION: CDRL3 of L88k

<400> SEQUENCE: 83

Phe Gln Gly Ser His Val Pro Phe Thr
1               5

<210> SEQ ID NO 84
<211> LENGTH: 11
<212> TYPE: PRT
<213> ORGANISM: Artificial Sequence
<220> FEATURE:
<223> OTHER INFORMATION: CDRL1 of L112k

<400> SEQUENCE: 84

Arg Ala Ser Gln Asp Ile Ser Asn Tyr Leu Asn
1               5                   10

<210> SEQ ID NO 85
<211> LENGTH: 7
<212> TYPE: PRT
<213> ORGANISM: Artificial Sequence
<220> FEATURE:
<223> OTHER INFORMATION: CDRL2 of L112k

<400> SEQUENCE: 85

Tyr Thr Ser Arg Leu His Ser
1               5

<210> SEQ ID NO 86
<211> LENGTH: 9
<212> TYPE: PRT
<213> ORGANISM: Artificial Sequence
<220> FEATURE:
<223> OTHER INFORMATION: CDRL3 of L112k

<400> SEQUENCE: 86

Gln Gln Gly Asn Thr Leu Arg Ser Arg
1               5

<210> SEQ ID NO 87
<211> LENGTH: 11
<212> TYPE: PRT
<213> ORGANISM: Artificial Sequence
<220> FEATURE:
<223> OTHER INFORMATION: CDRL1 of L116k

<400> SEQUENCE: 87
```

```
Lys Ala Ser Gln Asp Ile Asp Lys Tyr Ile Ala
1               5                   10

<210> SEQ ID NO 88
<211> LENGTH: 7
<212> TYPE: PRT
<213> ORGANISM: Artificial Sequence
<220> FEATURE:
<223> OTHER INFORMATION: CDRL2 of L116k

<400> SEQUENCE: 88

Tyr Thr Ser Thr Leu Gln Pro
1               5

<210> SEQ ID NO 89
<211> LENGTH: 9
<212> TYPE: PRT
<213> ORGANISM: Artificial Sequence
<220> FEATURE:
<223> OTHER INFORMATION: CDRL3 of L116k

<400> SEQUENCE: 89

Leu Gln Tyr Asp Asn Leu Leu Leu Thr
1               5

<210> SEQ ID NO 90
<211> LENGTH: 17
<212> TYPE: PRT
<213> ORGANISM: Artificial Sequence
<220> FEATURE:
<223> OTHER INFORMATION: CDRL1 of L129k

<400> SEQUENCE: 90

Lys Ser Ser Gln Ser Leu Leu Asn Ser Gly Asn Gln Lys Asn Tyr Leu
1               5                   10                  15

Ala

<210> SEQ ID NO 91
<211> LENGTH: 7
<212> TYPE: PRT
<213> ORGANISM: Artificial Sequence
<220> FEATURE:
<223> OTHER INFORMATION: CDRL2 of L129k

<400> SEQUENCE: 91

Gly Ala Ser Thr Arg Glu Ser
1               5

<210> SEQ ID NO 92
<211> LENGTH: 9
<212> TYPE: PRT
<213> ORGANISM: Artificial Sequence
<220> FEATURE:
<223> OTHER INFORMATION: CDRL3 of L129k

<400> SEQUENCE: 92

Gln Asn Asp His Ser Tyr Pro Leu Thr
1               5

<210> SEQ ID NO 93
<211> LENGTH: 132
<212> TYPE: PRT
<213> ORGANISM: Artificial Sequence
<220> FEATURE:
<223> OTHER INFORMATION: VH of #25 antibody
```

```
<400> SEQUENCE: 93

Met Gly Trp Thr Trp Ile Phe Ile Leu Ile Leu Ser Val Thr Thr Gly
 1               5                  10                  15

Val His Ser Glu Val Gln Leu Gln Gln Ser Gly Pro Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser Asn Gly Lys Ser Leu
    50                  55                  60

Glu Trp Ile Gly Asn Ile Asp Pro Tyr Tyr Gly Thr Ser Tyr Asn
65                  70                  75                  80

Gln Lys Phe Lys Gly Lys Ala Thr Leu Thr Val Asp Lys Ser Ser
                85                  90                  95

Thr Ala Tyr Met Gln Leu Lys Ser Leu Thr Ser Glu Asp Ser Ala Val
                100                 105                 110

Tyr Tyr Cys Ala Arg Ser Gly Thr Ala Trp Phe Ala Tyr Trp Gly Gln
            115                 120                 125

Gly Thr Leu Val
        130

<210> SEQ ID NO 94
<211> LENGTH: 138
<212> TYPE: PRT
<213> ORGANISM: Artificial Sequence
<220> FEATURE:
<223> OTHER INFORMATION: VL of #25 antibody

<400> SEQUENCE: 94

Met Glu Leu Gly Leu Ser Trp Val Phe Leu Val Thr Leu Leu Asn Gly
 1               5                  10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Thr Leu Arg Ala Glu Asp Ser
                100                 105                 110

Ala Thr Tyr Tyr Cys Ala Arg Asp Pro Thr Ile Gly Thr Val Leu Cys
            115                 120                 125

Tyr Gly Leu Leu Gly Ser Arg Asn Leu Ser
        130                 135

<210> SEQ ID NO 95
<211> LENGTH: 159
<212> TYPE: PRT
<213> ORGANISM: Artificial Sequence
<220> FEATURE:
<223> OTHER INFORMATION: VH of #28 antibody

<400> SEQUENCE: 95

Met Glu Leu Gly Leu Asn Trp Val Phe Leu Val Thr Leu Leu Asn Gly
 1               5                  10                  15
```

```
Ile Gln Cys Glu Val Lys Leu Val Glu Ser Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Ser Trp Val Arg Gln Pro Pro Gly Lys Ala Leu
 50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Thr Leu Arg Ala Glu Asp Ser
            100                 105                 110

Ala Thr Tyr Tyr Cys Ala Arg Asp Pro Thr Ile Gly Thr Val Leu Cys
        115                 120                 125

Tyr Gly Leu Leu Gly Ser Arg Asn Leu Ser His Arg Leu Leu Arg Glu
130                 135                 140

Ser Val Leu Pro Ile Arg Leu Ser Pro Gly Pro Trp Lys Leu Gly
145                 150                 155

<210> SEQ ID NO 96
<211> LENGTH: 126
<212> TYPE: PRT
<213> ORGANISM: Artificial Sequence
<220> FEATURE:
<223> OTHER INFORMATION: VL of #28 antibody

<400> SEQUENCE: 96

Met Asp Phe Gln Val Gln Ile Ile Ser Phe Leu Leu Ile Ser Ala Ser
 1               5                  10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Ser Cys Ser Ala Ser
        35                  40                  45

Ser Ser Val Ser Tyr Met Tyr Trp Tyr Gln Gln Lys Pro Gly Ser Ser
 50                  55                  60

Pro Lys Pro Trp Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Tyr
            100                 105                 110

His Ser Tyr Pro Phe Thr Phe Gly Ser Gly Thr Lys Trp Lys
        115                 120                 125

<210> SEQ ID NO 97
<211> LENGTH: 140
<212> TYPE: PRT
<213> ORGANISM: Artificial Sequence
<220> FEATURE:
<223> OTHER INFORMATION: VH of #77 antibody

<400> SEQUENCE: 97

Met Gly Trp Val Trp Thr Leu Pro Phe Leu Met Ala Ala Ala Gln Ser
 1               5                  10                  15

Ile Gln Ala Gln Ile Gln Leu Val His Ser Gly Pro Glu Leu Lys Lys
            20                  25                  30

Pro Gly Glu Thr Val Lys Ile Ser Cys Lys Ala Ser Gly Tyr Thr Phe
        35                  40                  45
```

Thr Asp Tyr Ser Met His Trp Val Lys Gln Ala Pro Gly Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Met Tyr Asp Tyr Ser Tyr Tyr Phe Asp Tyr Trp
        115                 120                 125

Gly Gln Gly Thr Thr Leu Thr Val Ser Ser Ala Lys
    130                 135                 140

<210> SEQ ID NO 98
<211> LENGTH: 132
<212> TYPE: PRT
<213> ORGANISM: Artificial Sequence
<220> FEATURE:
<223> OTHER INFORMATION: VL of #77 antibody

<400> SEQUENCE: 98

Met Ser Val Leu Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
                20                  25                  30

Val Ser Val Gly Glu Thr Val Thr Ile Thr Cys Arg Ala Ser Glu Asn
            35                  40                  45

Ile Tyr Ser Asn Leu Ala Trp Tyr Gln Gln Lys Gln Gly Lys Ser Pro
        50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Gly Thr Lys Leu Glu Ile Lys Arg
        115                 120                 125

Ala Asp Ala Ala
    130

<210> SEQ ID NO 99
<211> LENGTH: 137
<212> TYPE: PRT
<213> ORGANISM: Artificial Sequence
<220> FEATURE:
<223> OTHER INFORMATION: VH of #88 antibody

<400> SEQUENCE: 99

Met Glu Leu Gly Val Ser Trp Val Phe Leu Val Leu Leu Lys Gly
1               5                   10                  15

Val Gln Cys Glu Val Met Leu Val Glu Ser Gly Gly Gly Leu Val Lys
                20                  25                  30

Pro Gly Gly Ser Leu Lys Leu Ser Cys Thr Val Ser Gly Phe Thr Phe
            35                  40                  45

Ser Gly Tyr Ala Met Ser Trp Val Arg Gln Thr Pro Glu Lys Arg Leu
        50                  55                  60

Glu Trp Val Ala Ser Ile Thr Ser Gly Gly Ser Tyr Thr Ser Tyr Pro

```
                    65                  70                  75                  80
Asp Asn Met Lys Gly Arg Leu Thr Ile Ser Arg Asp Asn Asp Arg Asn
                    85                  90                  95

Thr Leu Asp Leu Gln Met Ser Ser Leu Arg Ser Glu Asp Thr Ala Met
                   100                 105                 110

Tyr Phe Cys Thr Arg His Ser Pro Val Ile Ala Ser Trp Phe Ala Tyr
                   115                 120                 125

Trp Gly Gln Gly Thr Leu Val His Cys
                   130                 135

<210> SEQ ID NO 100
<211> LENGTH: 136
<212> TYPE: PRT
<213> ORGANISM: Artificial Sequence
<220> FEATURE:
<223> OTHER INFORMATION: VL of #88 antibody

<400> SEQUENCE: 100

Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
                35                  40                  45

Val His Ser Asn Gly Asn Thr Tyr Leu Glu Trp Tyr Leu Gln Lys Pro
                50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Met Gly Val Tyr Tyr Cys
                   100                 105                 110

Phe Gln Gly Ser His Val Pro Phe Thr Phe Gly Ser Gly Thr Lys Leu
                   115                 120                 125

Glu Ile Lys Arg Ala Asp Ala Ala
                   130                 135

<210> SEQ ID NO 101
<211> LENGTH: 147
<212> TYPE: PRT
<213> ORGANISM: Artificial Sequence
<220> FEATURE:
<223> OTHER INFORMATION: VH of #112 antibody
<220> FEATURE:
<221> NAME/KEY: VARIANT
<222> LOCATION: (137)
<223> OTHER INFORMATION: any amino acids
<220> FEATURE:
<221> NAME/KEY: VARIANT
<222> LOCATION: (141)
<223> OTHER INFORMATION: any amino acids
<220> FEATURE:
<221> NAME/KEY: VARIANT
<222> LOCATION: (145)
<223> OTHER INFORMATION: any amino acids

<400> SEQUENCE: 101

Met Gly Arg Leu Thr Ser Ser Phe Leu Leu Leu Ile Val Pro Ala Tyr
 1               5                  10                  15

Val Leu Ser Gln Val Thr Leu Lys Glu Ser Gly Pro Gly Ile Leu Lys
                20                  25                  30
```

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
 50                  55                  60

Gly Leu Glu Trp Leu Ala His Ile Trp Trp Asp Asp Lys Phe Tyr
 65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
               100                 105                 110

Thr Tyr Tyr Cys Ala Arg Arg Ala Phe Ser Ser Ala Trp Phe Ala
               115                 120                 125

Tyr Trp Gly Pro Arg Asp Ser Gly Xaa Leu Ser Leu Xaa Ala Lys Asn
130                 135                 140

Xaa Pro Pro
145

<210> SEQ ID NO 102
<211> LENGTH: 125
<212> TYPE: PRT
<213> ORGANISM: Artificial Sequence
<220> FEATURE:
<223> OTHER INFORMATION: VL of #112 antibody

<400> SEQUENCE: 102

Met Val Ser Ser Ala Gln Phe Leu Gly Leu Leu Leu Cys Phe Gln
 1                   5                  10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Ile Ser Asn Tyr Leu Asn Trp Tyr Gln Gln Lys Pro Asp Gly Thr Val
 50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
               100                 105                 110

Thr Leu Arg Ser Arg Ser Val Leu Gly Pro Ser Trp Ser
               115                 120                 125

<210> SEQ ID NO 103
<211> LENGTH: 143
<212> TYPE: PRT
<213> ORGANISM: Artificial Sequence
<220> FEATURE:
<223> OTHER INFORMATION: VH of #116 antibody

<400> SEQUENCE: 103

Met Glu Trp Thr Trp Val Ile Leu Phe Leu Leu Ser Ile Thr Ala Gly
 1                   5                  10                  15

Val His Cys Gln Val Gln Leu Gln Gln Ser Gly Pro Glu Leu Val Lys
                20                  25                  30

Pro Gly Ala Ser Val Lys Ile Ser Cys Lys Ala Ser Gly Tyr Ala Phe
            35                  40                  45

Ser Ser Ser Trp Met Asn Trp Val Lys Gln Arg Pro Gly Gln Gly Leu
 50                  55                  60

```
Glu Trp Ile Gly Arg Ile Tyr Pro Gly Asp Gly Asp Thr Asn Tyr Asn
 65                  70                  75                  80

Gly Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Val Asp Ser Ala Val
            100                 105                 110

Tyr Phe Cys Ala Arg Ile Gly Asn Tyr Tyr Gly Ser Ser Tyr Leu Tyr
            115                 120                 125

Trp Tyr Phe Asp Val Trp Gly Ala Gly Thr Thr Val Thr Val Ser
            130                 135                 140

<210> SEQ ID NO 104
<211> LENGTH: 131
<212> TYPE: PRT
<213> ORGANISM: Artificial Sequence
<220> FEATURE:
<223> OTHER INFORMATION: VL of #116 antibody

<400> SEQUENCE: 104

Met Arg Gln Ser Ile Gln Phe Leu Gly Leu Leu Leu Phe Trp Leu His
 1               5                  10                  15

Gly Ala Gln Cys Asp Ile Gln Met Thr Gln Ser Pro Ser Ser Leu Ser
                 20                  25                  30

Ala Ser Leu Gly Gly Lys Val Thr Ile Thr Cys Lys Ala Ser Gln Asp
            35                  40                  45

Ile Asp Lys Tyr Ile Ala Trp Tyr Gln His Arg Pro Gly Lys Gly Pro
        50                  55                  60

Ser Leu Leu Ile His Tyr Thr Ser Thr Leu Gln Pro Gly Ile Pro Ser
 65                  70                  75                  80

Arg Phe Ser Gly Ser Gly Ser Gly Lys Asn Tyr Ser Phe Ser Ile Ser
                 85                  90                  95

Asn Leu Glu Pro Glu Asp Ile Ala Thr Tyr Tyr Cys Leu Gln Tyr Asp
            100                 105                 110

Asn Leu Leu Leu Thr Phe Gly Ala Gly Thr Lys Leu Glu Leu Lys Arg
            115                 120                 125

Ala Asp Ala
    130

<210> SEQ ID NO 105
<211> LENGTH: 138
<212> TYPE: PRT
<213> ORGANISM: Artificial Sequence
<220> FEATURE:
<223> OTHER INFORMATION: VH of #129 antibody

<400> SEQUENCE: 105

Met Ala Val Leu Val Leu Phe Phe Cys Leu Val Thr Phe Pro Ser Cys
 1               5                  10                  15

Val Leu Ser Gln Val Gln Leu Lys Gln Ser Gly Pro Gly Leu Val Gln
                 20                  25                  30

Pro Ser Gln Ser Leu Ser Ile Thr Cys Thr Val Ser Gly Phe Ser Leu
            35                  40                  45

Thr Ser Tyr Gly Val His Trp Val Arg Gln Ser Pro Gly Lys Gly Leu
        50                  55                  60

Glu Trp Leu Gly Val Ile Trp Ser Gly Gly Ser Thr Asp Tyr Asn Ala
 65                  70                  75                  80

Ala Phe Ile Ser Arg Leu Ser Ile Ser Lys Asp Asn Ser Lys Ser Gln
```

```
                        85                  90                  95
Val Phe Phe Lys Met Asn Ser Leu Gln Ala Asn Asp Thr Ala Ile Tyr
                100                 105                 110

Tyr Cys Ala Arg Asn Trp Gly Ala Met Asp Tyr Trp Gly Gln Gly Thr
        115                 120                 125

Ser Val Thr Val Ser Ser Glu Ser Gln Ser
        130                 135

<210> SEQ ID NO 106
<211> LENGTH: 133
<212> TYPE: PRT
<213> ORGANISM: Artificial Sequence
<220> FEATURE:
<223> OTHER INFORMATION: VL of #129 antibody

<400> SEQUENCE: 106

Met Val Leu Met Ser Leu Leu Phe Trp Val Ser Gly Thr Cys Gly Asp
 1               5                  10                  15

Ile Val Met Thr Gln Ser Pro Ser Ser Leu Ser Val Ser Ala Gly Glu
            20                  25                  30

Lys Val Thr Met Ser Cys Lys Ser Ser Gln Ser Leu Leu Asn Ser Gly
        35                  40                  45

Asn Gln Lys Asn Tyr Leu Ala Trp Tyr Gln Gln Lys Pro Gly Gln Pro
    50                  55                  60

Pro Lys Leu Leu Ile Tyr Gly Ala Ser Thr Arg Glu Ser Gly Val Pro
65                  70                  75                  80

Asp Arg Phe Thr Gly Ser Gly Ser Gly Thr Asp Phe Thr Leu Thr Ile
                85                  90                  95

Ser Ser Val Gln Ala Glu Asp Leu Ala Val Tyr Tyr Cys Gln Asn Asp
                100                 105                 110

His Ser Tyr Pro Leu Thr Phe Gly Ala Gly Thr Lys Leu Glu Leu Lys
        115                 120                 125

Arg Ala Asp Ala Ala
        130

<210> SEQ ID NO 107
<211> LENGTH: 396
<212> TYPE: DNA
<213> ORGANISM: Artificial Sequence
<220> FEATURE:
<223> OTHER INFORMATION: VH coding nucleotide (#25 antibody)

<400> SEQUENCE: 107
atgggatgga cctggatctt tatcttaatc ctgtcagtaa ctacaggtgt ccactctgag     60
gtccagctgc agcagtctgg acctgagctg gagaagcctg gcgcttcagt gaagatatcc    120
tgcaaggctt ctggttactc attcactggc tacaacatga actgggtgaa gcagagcaat    180
ggaaagagcc ttgagtggat tggaaatatt gatccttact atggtggtac tagctacaac    240
cagaagttca gggcaaggc cacattgact gtagacaaat cctccagcac agcctacatg     300
cagctcaaga gcctgacatc tgaggactct gcagtctatt actgtgcaag atctgggacg    360
gcctggtttg cttactgggg ccaagggact ctggtc                              396

<210> SEQ ID NO 108
<211> LENGTH: 477
<212> TYPE: DNA
<213> ORGANISM: Artificial Sequence
<220> FEATURE:
<223> OTHER INFORMATION: VH coding nucleotide (#28 antibody)
```

-continued

```
<400> SEQUENCE: 108
atggagttgg ggttaaactg ggttttcctt gtaacacttt taaatggtat ccagtgtgag      60
gtgaagctgg tggagtctgg aggaggcttg gtacagcctg ggggttctct gagactctcc     120
tgtgcaactt ctgggttcac cttcactgat tactacatga gctgggtccg ccagcctcca     180
ggaaaggcac ttgagtggtt gggttttatt agaaacaaag ctaatggtta cacaacagag     240
tacagtgcat ctgtgaaggg tcggttcacc atctccagag ataattccca aagcatcctc     300
tatcttcaaa tgaacaccct gagagctgag acagtgcca cttattactg tgcaagagat      360
cctactatag gtaccgtact atgctatgga ctactgggt caaggaacct cagtcaccgt       420
ctcctcagag agtcagtcct tcccatccgt ctatcccctg gtccctggaa gcttggg         477

<210> SEQ ID NO 109
<211> LENGTH: 420
<212> TYPE: DNA
<213> ORGANISM: Artificial Sequence
<220> FEATURE:
<223> OTHER INFORMATION: VH coding nucleotide (#77 antibody)

<400> SEQUENCE: 109
atgggttggg tgtggacctt gccattcctg atggcagctg cccaaagtat ccaagcacag      60
atccagttgg tgcactctgg acctgagctg aagaagcctg gagagacagt caagatctcc     120
tgcaaggctt ctggttatac cttcacagac tattcaatgc actgggtgaa gcaggctcca     180
ggaaagggtt taaagtggat gggctggata aacactgaga ctggtgagcc aacatatgca     240
gatgacttca agggacggtt tgccttctct ttggaaacct ctgccagcac tgcctatttg     300
cagatcaaca acctcaaaaa tgaggacacg gctacatatt tctgtgctag gatgtatgat     360
tattcgtact actttgacta ctggggccaa ggcaccactc tcacagtctc ctcagccaaa     420

<210> SEQ ID NO 110
<211> LENGTH: 411
<212> TYPE: DNA
<213> ORGANISM: Artificial Sequence
<220> FEATURE:
<223> OTHER INFORMATION: VH coding nucleotide (#88 antibody)

<400> SEQUENCE: 110
atggagttgg gggtaagctg ggttttcctt gtccttgttt taaaaggtgt ccagtgtgaa     60
gtgatgctgg tggagtctgg gggaggcttg gtgaagcctg gagggtccct gaaactctcc    120
tgtacagtct ctggattcac tttcagtggg tatgccatgt cttgggttcg ccagactccg    180
gagaagaggc tggagtgggt cgcatccatt acttctggtg gtagttatac ttcctatcca    240
gacaatatga agggcgact caccatctcc agagacaatg acggaacac cctggacctg      300 caaatgagca gtctgaggtc tgaggacacg gccatgtatt tctgtacaag acactcacct    360
gtgattgcct cctggtttgc ttactggggc caagggactc tggtccactg t             411

<210> SEQ ID NO 111
<211> LENGTH: 441
<212> TYPE: DNA
<213> ORGANISM: Artificial Sequence
<220> FEATURE:
<223> OTHER INFORMATION: VH coding nucleotide (#112 antibody)
<220> FEATURE:
<221> NAME/KEY: variation
<222> LOCATION: (410)
<223> OTHER INFORMATION: a,t,c or g
<220> FEATURE:
```

<221> NAME/KEY: variation
<222> LOCATION: (411)
<223> OTHER INFORMATION: a,t,c or g
<220> FEATURE:
<221> NAME/KEY: variation
<222> LOCATION: (422)
<223> OTHER INFORMATION: a,t,c or g
<220> FEATURE:
<221> NAME/KEY: variation
<222> LOCATION: (434)
<223> OTHER INFORMATION: a,t,c or g

<400> SEQUENCE: 111

| | |
|---|---|
| atgggcaggc ttacttcttc attcctgctg ctgattgtcc ctgcatatgt cttgtcccaa | 60 |
| gttactctaa aagagtctgg ccctgggata ttgaagccct cacagaccct cagtctgact | 120 |
| tgttctttct ctgggttttc actgagcact tctggtatgg gtgtaggctg gattcgtcag | 180 |
| ccttcaggga agggtctgga gtggctggca cacatttggt gggatgatga taagttctat | 240 |
| aacccatccc tgaagagcca gctcacaatc tccaaggata cctccagaaa ccaggtattc | 300 |
| ctcaagatca ccagtgtgga cactgcagat actgccactt actactgtgc tcgaagagca | 360 |
| tttagtagct ctgcctggtt tgcttactgg ggcccaaggg actctggtcn nctgtctctg | 420 |
| cnagccaaaa acanccccccc c | 441 |

<210> SEQ ID NO 112
<211> LENGTH: 429
<212> TYPE: DNA
<213> ORGANISM: Artificial Sequence
<220> FEATURE:
<223> OTHER INFORMATION: VH coding nucleotide (#116 antibody)

<400> SEQUENCE: 112

| | |
|---|---|
| atggaatgga cctgggtcat tctcttcctc ctgtcaataa ctgcaggtgt ccattgccag | 60 |
| gtccagctgc agcagtctgg acctgagctg gtgaagcctg gggcctcagt gaagatttcc | 120 |
| tgcaaagctt ctggctacgc attcagtagc tcttggatga actgggtgaa gcagaggcct | 180 |
| ggacagggtc ttgagtggat tggacggatt tatcctggag atggagatac taactacaat | 240 |
| gggaagttca aggcaaggc cacactgact gcagacaaat cctccagcac agcctacatg | 300 |
| cagctcagca gcctgacctc tgtggactct gcggtctatt tctgtgcaag aatagggaat | 360 |
| tactacggta gtagctacct ctactggtac ttcgatgtct ggggcgcagg gaccacggtc | 420 |
| accgtctct | 429 |

<210> SEQ ID NO 113
<211> LENGTH: 414
<212> TYPE: DNA
<213> ORGANISM: Artificial Sequence
<220> FEATURE:
<223> OTHER INFORMATION: VH coding nucleotide (#129 antibody)

<400> SEQUENCE: 113

| | |
|---|---|
| atggctgtct tggtgctgtt cttctgcctg gtgacattcc caagctgtgt cctatcccag | 60 |
| gtgcagctga agcagtcagg acctggccta gtgcagccct cacagagcct gtccatcacc | 120 |
| tgcacagtct ctggtttctc attaactagc tatggtgtac actgggttcg ccagtctcca | 180 |
| ggaaagggtc tggagtggct gggagtgata tggagtggtg gaagcacaga ctataatgca | 240 |
| gctttcatat ccagactgag catcagcaag gacaattcca agagccaagt tttctttaaa | 300 |
| atgaacagtc tgcaagctaa tgacacagcc atatattact gtgccagaaa ttggggggct | 360 |
| atggactact ggggtcaagg aacctcagtc accgtctcct cagagagtca gtct | 414 |

<210> SEQ ID NO 114
<211> LENGTH: 393
<212> TYPE: DNA
<213> ORGANISM: Artificial Sequence
<220> FEATURE:
<223> OTHER INFORMATION: VL coding nucleotide (#25 antibody)

<400> SEQUENCE: 114

```
atgagtgtgc tcactcaggt cctggggttg ctgctgctgt ggcttacagg tgccagatgt    60
gacatccaga tgactcagtc tccagcctcc ctatctgcat ctgtgggaga aactgtcacc   120
atcacatgtc gagcaagtgg gaatattcac aattatttag catggtatca gcagaaacag   180
ggaaaatctc ctcagctcct ggtctataat gcaaaaacct tagcagatgg tgtgccatca   240
aggttcagtg gcagtggatc aggaacacaa tattctctca agatcaacag cctgcagcct   300
gaagattttg ggagttatta ctgtcaacat ttttggagta ctccattcac gttcggctcg   360
gggacaaagt ggaaataaaa cgggctgatg ctg                                393
```

<210> SEQ ID NO 115
<211> LENGTH: 378
<212> TYPE: DNA
<213> ORGANISM: Artificial Sequence
<220> FEATURE:
<223> OTHER INFORMATION: VL coding nucleotide (#28 antibody)

<400> SEQUENCE: 115

```
atggattttc aggtgcagat tatcagcttc ctgctaatca gtgcctcagt cataatgtcc    60
agaggacaaa ttgttctcac ccagtctcca gcaatcatgt ctgcatctcc aggggagaag   120
gtcaccatat cctgcagtgc cagctcaagt gtaagttaca tgtactggta ccagcagaag   180
ccaggatcct cccccaaacc ctggatttat cgcacatcca acctggcttc tggagtccct   240
gctcgcttca gtggcagtgg gtctgggacc tcttactctc tcacaatcag cagcatggag   300
gctgaagatg ctgccactta ttactgccag cagtatcata gttacccatt cacgttcggc   360
tcggggacaa agtggaaa                                                 378
```

<210> SEQ ID NO 116
<211> LENGTH: 396
<212> TYPE: DNA
<213> ORGANISM: Artificial Sequence
<220> FEATURE:
<223> OTHER INFORMATION: VL coding nucleotide (#77 antibody)

<400> SEQUENCE: 116

```
atgagtgtgc tcactcaggt cctggggttg ctgctgctgt ggcttacaga tgccagatgt    60
gacatccaga tgactcagtc tccagcctcc ctatctgtat ctgtgggaga aactgtcacc   120
atcacatgtc gagcaagtga gaatatttac agtaatttag catggtatca gcagaaacag   180
ggaaaatctc ctcagctcct ggtctatgct gcaacaaact tagcagatgg tgtgccatca   240
aggttcagtg gcagtggatc aggcacacag tattccctca gatcaacag cctgcagtct    300 gaagattttg ggagttatta ctgtcaacat ttttggggta ctccgtacac gttcggggg    360 gggaccaagc tggaaataaa acgggctgat gctgcc                             396
```

<210> SEQ ID NO 117
<211> LENGTH: 408
<212> TYPE: DNA
<213> ORGANISM: Artificial Sequence
<220> FEATURE:

<223> OTHER INFORMATION: VL coding nucleotide (#88 antibody)

<400> SEQUENCE: 117

```
atgaagttgc ctgttaggct gttggtgctg atgttctgga ttcctgcttc cagcagtgat    60
gttttgatga cccaaactcc actctccctg cctgtcagtc ttggagatca agcctccatc   120
tcttgcagat ctagtcagag cattgtacat agtaatggaa acacctattt agaatggtac   180
ctgcagaaac caggccagtc tccaaagctc ctgatctaca agtttccaa ccgattttct    240
ggggtcccag acaggttcag tggcagtgga tcaggacag atttcacact caagatcagc    300
agagtggagg ctgaggatat gggagtttat tactgctttc aaggttcaca tgttccattc   360
acgttcggct cggggacaaa gttggaaata aaacgggctg atgctgca                408
```

<210> SEQ ID NO 118
<211> LENGTH: 375
<212> TYPE: DNA
<213> ORGANISM: Artificial Sequence
<220> FEATURE:
<223> OTHER INFORMATION: VL coding nucleotide (#112 antibody)

<400> SEQUENCE: 118

```
atggtgtcct cagctcagtt ccttggtctc ctgttgctct gttttcaagg taccagatgt    60
gatatccaga tgacacagac tacatcctcc ctgtctgcct ctctgggaga cagagtcacc   120
atcagttgca gggcaagtca ggacattagc aattatttaa actggtatca gcagaaacca   180
gatggaactg ttaaactcct gatctactac acatcaagat tacactcagg agtcccatca   240
aggttcagtg gcagtgggtc tggaacagat tattctctca ccattagcaa cctggagcaa   300
gaagatattg ccacttactt ttgccaacag gtaatacgc ttcgctcacg ttcggtgctg    360
ggaccaagct ggagc                                                    375
```

<210> SEQ ID NO 119
<211> LENGTH: 393
<212> TYPE: DNA
<213> ORGANISM: Artificial Sequence
<220> FEATURE:
<223> OTHER INFORMATION: VL coding nucleotide (#116 antibody)

<400> SEQUENCE: 119

```
atgaggcagt cgattcagtt cctggggctc ttgttgttct ggcttcatgg tgctcagtgt    60
gacatccaga tgacacagtc tccatcctca ctgtctgcat ctctgggagg caaagtcacc   120
atcacttgca aggcaagcca agacattgac aagtatatag cttggtacca acacaggcct   180
ggaaaaggtc ctagtctgct catacattac acatctacat tacagccagg catcccatca   240
aggttcagtg gaagtgggtc tgggaaaaat tattccttca gcatcagcaa cctggagcct   300
gaagatattg caacttatta ttgtctacag tatgataatc ttctgctcac gttcggtgct   360
gggaccaagc tggagctgaa acgggctgat gct                                393
```

<210> SEQ ID NO 120
<211> LENGTH: 399
<212> TYPE: DNA
<213> ORGANISM: Artificial Sequence
<220> FEATURE:
<223> OTHER INFORMATION: VL coding nucleotide (#129 antibody)

<400> SEQUENCE: 120

```
atggttctta tgtccttgct gttctgggta tctggtacct gtgggacat tgtgatgaca     60
cagtctccat cctccctgag tgtgtcagca ggagagaagg tcactatgag ctgcaagtcc   120
```

-continued

```
agtcagagtc tgttaaacag tggaaatcaa aagaactact tggcctggta ccagcagaaa      180
ccagggcagc ctcctaaact gttgatctac ggggcatcca ctagggaatc tggggtccct      240
gatcgcttca caggcagtgg atctggaacc gatttcactc ttaccatcag cagtgtgcag      300
gctgaagacc tggcagttta ttactgtcag aatgatcata gttatcctct cacgttcggt      360
gctgggacca agctggagct gaaacgggct gatgctgcc                             399
```